United States Patent [19]
Lee et al.

[11] Patent Number: 6,096,506
[45] Date of Patent: Aug. 1, 2000

[54] ANTIBODIES SPECIFIC FOR GROWTH DIFFERENTIATION FACTOR-8 AND METHODS OF USING SAME

[75] Inventors: Se-Jin Lee; Alexandra C. McPherron, both of Baltimore, Md.

[73] Assignee: The Johns Hopkins University School of Medicine, Baltimore, Md.

[21] Appl. No.: 09/177,860

[22] Filed: Oct. 23, 1998

Related U.S. Application Data

[60] Division of application No. 08/525,596, filed as application No. PCT/US94/03019, Mar. 18, 1994, Pat. No. 5,827,733, and a continuation-in-part of application No. 08/033,923, Mar. 19, 1993, abandoned.

[51] Int. Cl.$^7$ ............................ C07K 16/22; G01N 33/53
[52] U.S. Cl. .................... 435/7.1; 530/387.1; 530/387.9; 530/388.1; 530/388.15; 530/388.24; 530/389.1; 530/389.2
[58] Field of Search ............................. 530/387.1, 387.9, 530/388.1, 388.15, 388.24, 389.1, 389.2; 435/7.1

[56] References Cited

U.S. PATENT DOCUMENTS 5,827,733 10/1998 Lee et al. ................................. 435/325

OTHER PUBLICATIONS

Bowie et al. Science 247:1307–1310, 1990.
Rudinger, Peptide Hormones, Parsons, ed., University Park Press, Baltimore, pp. 1–7, 1976.
Wells, Biochemistry 29:8507–8517, 1990.
Ngo et al. The Protein Folding Problem and Tertiary Structure Prediction. Merz et al., eds., Birkhauser, Boston, pp. 491–495, 1990
Callard et al. The Cytokine FactsBook, Academic Press, London, pp. 31–32, 1994.
Jones, et al., "Isolation of Vgr-2, a Novel Member of the Transforming Growth Factor–β–Related Gene Family," *Molecular Endocrinology* vol. 6 No. 11, pp. 1961–1968, 1992.
Se–Jin Lee, "Expression of growth/differentiation factor 1 in the nervous system: Conservation of a bicistronic structure," *Proc. Natl. Acad. Sci. USA* vol. 88, pp. 4250–4254, May 1991.
Se–Jin Lee, "Identification of a Novel Member (GDF–1) of the Transforming Growth Factor–β Superfamily," *Molecular Endocrinology* vol. 4, pp. 1034–1040, 1990.
Alexandra C. McPherron and Se–Jin Lee, "GDF–3 and GDF–9: Two New Members of the Transforming Growth Factor–β Superfamily Containing a Novel Pattern of Cysteines," *The Journal of Biological Chemistry*, vol. 268, No. 5, pp. 3444–3449, 1993.

*Primary Examiner*—Elizabeth Kemmerer
*Attorney, Agent, or Firm*—Gray Cary Ware & Freidenrich LLP; Lisa A. Haile

[57] ABSTRACT

Growth differentiation factor-8 (GDF-8) is disclosed along with its polynucleotide sequence and amino acid sequence. Also disclosed are diagnostic and therapeutic methods of using the GDF-8 polypeptide and polynucleotide sequences.

14 Claims, 15 Drawing Sheets

```
  1  TTAAGGTAGGAAGGATTTCAGGCTCTATTTACATAATTGTTCTTTCCTTTTCACACAGAA   60
                                                               N
 61  TCCCTTTTTAGAAGTCAAGGTGACAGACACACCCAAGAGGTCCCGGAGAGACTTTGGGCT  120
      P  F  L  E  V  K  V  T  D  T  P [K  R] S [R  R] D  F  G  L
121  TGACTGCGATGAGCACTCCACGGAATCCCGGTGCTGCCGCTACCCCCTCACGGTCGATTT  180
      D  C  D  E  H  S  T  E  S  R  C  C  R  Y  P  L  T  V  D  F
181  TGAAGCCTTTGGATGGGACTGGATTATCGCACCCAAAAGATATAAGGCCAATTACTGCTC  240
      E  A  F  G  W  D  W  I  I  A  P  K  R  Y  K  A  N  Y  C  S
241  AGGAGAGTGTGAATTTGTGTTTTTACAAAAATATCCGCATACTCATCTTGTGCACCAAGC  300
      G  E  C  E  F  V  F  L  Q  K  Y  P  H  T  H  L  V  H  Q  A
301  AAACCCCAGAGGCTCAGCAGGCCCTTGCTGCACTCCGACAAAAATGTCTCCCATTAATAT  360
      N  P  R  G  S  A  G  P  C  C  T  P  T  K  M  S  P  I  N  M
361  GCTATATTTTAATGGCAAAGAACAAATAATATATGGGAAAATTCCAGCCATGGTAGTAGA  420
      L  Y  F  N  G  K  E  Q  I  I  Y  G  K  I  P  A  M  V  V  D
421  CCGCTGTGGGTGCTCATGAGCTTTGCATTAGGTTAGAAACTTCCCAAGTCATGGAAGGTC  480
      R  C  G  C  S  *
481  TTCCCCTCAATTTCGAAACTGTGAATTCCTGCAGCCCGGGGGATCCACTAGTTCTAGAGC  540
541  GGCCGCCACC  550
```

FIG.2a

```
  1  CAAAAAGATCCAGAAGGGATTTTGGTCTTGACTGTGATGAGCACTCAACAGAATCACGAT   60
     [K  R] S [R  R] D  F  G  L  D  C  D  E  H  S  T  E  S  R  C
 61  GCTGTCGTTACCCTCTAACTGTGGATTTTGAAGCTTTTGGATGGGATTGGATTATCGCTC  120
      C  R  Y  P  L  T  V  D  F  E  A  F  G  W  D  W  I  I  A  P
121  CTAAAAGATATAAGGCCAATTACTGCTCTGGAGAGTGTGAATTTGTATTTTTACAAAAAT  180
      K  R  Y  K  A  N  Y  C  S  G  E  C  E  F  V  F  L  Q  K  Y
181  ATCCTCATACTCATCTGGTACACCAAGCAAACCCCAGAGGTTCAGCAGGCCCTTGCTGTA  240
      P  H  T  H  L  V  H  Q  A  N  P  R  G  S  A  G  P  C  C  T
241  CTCCCACAAAGATGTCTCCAATTAATATGCTATATTTTAATGGCAAAGAACAAATAATAT  300
      P  T  K  M  S  P  I  N  M  L  Y  F  N  G  K  E  Q  I  I  Y
301  ATGGGAAAATTCCAGCGATGGTAGTA  326
      G  K  I  P  A  M  V  V
```

```
GDF-8        SRRDFGLDCDEHSTESRCCRYPLTVDF-EAFGWD-WIIAPKRYKANYCSGECEFVFLQKYP----------
GDF-1        RPRRDAEPVLGGGPGGACRARRLYVSF-REVGWHRWVIAPRGFLANYCQGQCALPVALSGSGGPP
BMP-2        REKRQAKHKQRKRLKSSCKRHPLYVDF-SDVGWNDWIVAPPGYHAFYCHGECPFPLADHLNS----
BMP-4        KRSPKHHSQRARKKNKNCRRHSLYVDF-SDVGWNDWIVAPPGYQAFYCHGDCPFPLADHLNS----
Vgr-1        SRGSGSSDYNGSELKTACKKHELYVSF-QDLGWQDWIIAPKGYAANYCDGECSFPLNAHMNA----
CP-1         LRMANVAENSSSDQRQACKKHELYVSF-RDLGWQDWIIAPEGYAAYYCEGECAFPLNSYMNA----
BMP-5        SRMSSVGDYNTSEQKQACKKHELYVSF-RDLGWQDWIIAPEGYAAFYCDGECSFPLNAHMNA----
BMP-3        EQTLKKARRKQWIEPRNCARRYLKVDF-ADIGWSEWIISPKSFDAYYCSGACQFPMPKSLKPS---
MIS          GPGRAQRSAGATAADGPCALRELSVDL------RAERSVLIPETYQANNCQGVCGWPQSDRNPRY-
Inhibinα     ALRLLQRPPEEPAAHANCHRVALNISF-QELGWERWIVYPPSFIFHYCHGGCGLHIPPNLSLPV--
InhibinβA    HRRRRRGLECDGKV-NICCKKQFFVSF-KDIGWNDWIIAPSGYHANYCEGECPSHIAGISGSSL--
InhibinβB    HRIRKRGLECDGRT-NLCCRQQFFIDF-RLIGWNDWIIAPTGYYGNYCEGSCPAYLAGVPGSAS--
TGF-β1       HRRALDTNYCFSSTEKNCCVRQLYIDFRKDLGWK-WIHEPKGYHANFCLGPCPYIWSLD-------
TGF-β2       KKRALDAAYCFRNVQDNCCLRPLYIDFKRDLGWK-WIHEPKGYNANFCAGACPYLWSSD-------
TGF-β3       KKRALDTNYCFRNLEENCCVRPLYIDFRQDLGWK-WVHEPKGYYANFCSGPCPYLRSAD-------

GDF-8        -HTHLVHQANPRG----------SAGPCCT----PTKMSPINMLYF-NGKEQIIYGKIPAMVVDRCGCS
GDF-1        ALNHAVLRALMHA----AAPGAADLPCCV----PARLSPISVLFF-DNSDNVVLRQYEDMVVDECGCR
BMP-2        -TNHAIVQTLVNS----VNSKIPKACCV----PTELSAISMLYL-DENEKVVLKNYQDMVVEGCGCR
BMP-4        -TNHAIVQTLVNS----VNSSIPKACCV----PTELSAISMLYL-DEYDKVVLKNYQEMVVEGCGCR
Vgr-1        -TNHAIVQTLVHL----MNPEYVPKPCCA----PTKLNAISVLYF-DDNSNVILKKYRNMVRACGCH
OP-1         -TNHAIVQTLVHF----INPETVPKPCCA----PTQLNAISVLYF-DDSSNVILKKYRNMVRACGCH
BMP-5        -TNHAIVQTLVHL----MFPDHVPKPCCA----PTKLNAISVLYF-DDSSNVILKKYRNMVRSCGCH
BMP-3        -NHATIQSIVRA-VGVVPGIPEPCCV----PEKMSSLSILFF-DENKNVVLKVYPNMTVESCACR
MIS          -GNHVVLLKMQA----RGAALARPPCCV----PTAYAGKLLISLSEER---ISAHHVPNMVATECGCR
Inhibinα     -PGAPPTPAQPYS----------LLPGAQPCCAALPGTMRPLHVRTTSDGGYSFKYETVPNLLTCHCACI
InhibinβA    -SFHSTVINHYRMRGHSPFANLKSCCV----PTKLRPMSMLYY-DDGQNIIKKDIQNMIVEECGCS
InhibinβB    -SFHTAVVNQYRMRGLNPGT-VNSCCI----PTKLSTMSMLYF-DDEYNIVKRDVPNMIVEECGCA
TGF-β1       -TQYSKVLALYNQ----HNPGASAAPCCV----PQALEPLPIVYY-VGRKPKV-EQLSNMIVRSCKCS
TGF-β2       -TQHSRVLSLYNT----INPEASASPCCV----SQDLEPLTILYY-IGKTPKI-EQLSNMIVKSCKCS
TGF-β3       -TTHSTVLGLYNT----LNPEASASPCCV----PQDLEPLTILYY-VGRTPKV-EQLSNMVVKSCKCS
```

FIG. 4

| | GDF-1 | GDF-2 | GDF-3 | GDF-5 | GDF-6 | GDF-7 | GDF-8 | GDF-9 | BMP-2 | BMP-4 | Vgr-1 | OP-1 | BMP-5 | BMP-3 | MIS | Inhibinα | InhibinβA | InhibinβB | TGF-β1 | TGF-β2 | TGF-β3 |
|---|---|---|---|---|---|---|---|---|---|---|---|---|---|---|---|---|---|---|---|---|---|
| GDF-1 | 100 | | | | | | | | | | | | | | | | | | | | |
| GDF-2 | 33 | 100 | | | | | | | | | | | | | | | | | | | |
| GDF-3 | 50 | 42 | 100 | | | | | | | | | | | | | | | | | | |
| GDF-5 | 46 | 47 | 49 | 100 | | | | | | | | | | | | | | | | | |
| GDF-6 | 44 | 51 | 49 | 86 | 100 | | | | | | | | | | | | | | | | |
| GDF-7 | 48 | 48 | 48 | 80 | 80 | 100 | | | | | | | | | | | | | | | |
| GDF-8 | 35 | 31 | 41 | 37 | 38 | 37 | 100 | | | | | | | | | | | | | | |
| GDF-9 | 27 | 32 | 33 | 33 | 34 | 33 | 33 | 100 | | | | | | | | | | | | | |
| BMP-2 | 42 | 52 | 53 | 57 | 57 | 57 | 41 | 33 | 100 | | | | | | | | | | | | |
| BMP-4 | 43 | 51 | 50 | 57 | 56 | 57 | 38 | 34 | 92 | 100 | | | | | | | | | | | |
| Vgr-1 | 46 | 55 | 53 | 51 | 53 | 52 | 45 | 31 | 61 | 60 | 100 | | | | | | | | | | |
| OP-1 | 47 | 52 | 50 | 51 | 53 | 53 | 42 | 30 | 60 | 58 | 87 | 100 | | | | | | | | | |
| BMP-5 | 46 | 55 | 50 | 52 | 54 | 52 | 42 | 31 | 61 | 59 | 91 | 88 | 100 | | | | | | | | |
| BMP-3 | 42 | 34 | 42 | 47 | 46 | 46 | 38 | 29 | 48 | 47 | 44 | 42 | 43 | 100 | | | | | | | |
| MIS | 34 | 20 | 22 | 27 | 26 | 25 | 31 | 21 | 27 | 27 | 24 | 27 | 24 | 30 | 100 | | | | | | |
| Inhibinα | 23 | 20 | 25 | 24 | 27 | 26 | 26 | 27 | 22 | 22 | 25 | 24 | 24 | 29 | 18 | 100 | | | | | |
| InhibinβA | 37 | 32 | 42 | 40 | 43 | 41 | 38 | 30 | 42 | 41 | 44 | 43 | 43 | 36 | 24 | 26 | 100 | | | | |
| InhibinβB | 35 | 25 | 41 | 37 | 39 | 36 | 42 | 31 | 42 | 42 | 41 | 42 | 37 | 37 | 25 | 25 | 63 | 100 | | | |
| TGF-β1 | 33 | 26 | 36 | 33 | 35 | 36 | 34 | 23 | 35 | 34 | 35 | 37 | 34 | 32 | 28 | 23 | 41 | 35 | 100 | | |
| TGF-β2 | 32 | 28 | 31 | 34 | 36 | 35 | 37 | 25 | 34 | 33 | 37 | 38 | 35 | 32 | 23 | 22 | 37 | 34 | 74 | 100 | |
| TGF-β3 | 33 | 30 | 32 | 37 | 38 | 38 | 37 | 25 | 36 | 35 | 39 | 38 | 36 | 32 | 25 | 24 | 36 | 37 | 78 | 82 | 100 |

```
   1  GTCTCTCGGACGGTACATGCACTAATATTTCACTTGGCATTACTCAAAAGCAAAAAGAAG    60
  61  AAATAAGAACAAGGGAAAAAAAAAGATTGTGCTGATTTTTAAAATGATGCAAAAACTGCA   120
                                               M  M  Q  K  L  Q
 121  AATGTATGTTTATATTTACCTGTTCATGCTGATTGCTGCTGGCCCAGTGGATCTAAATGA   180
       M  Y  V  Y  I  Y  L  F  M  L  I  A  A  G  P  V  D  L  N  E
 181  GGGCAGTGAGAGAGAAGAAAATGTGGAAAAAGAGGGGCTGTGTAATGCATGTGCCGTGGAG   240
       G  S  E  R  E  E  N  V  E  K  E  G  L  C  N  A  C  A  W  R
 241  ACAAAACACGAGGTACTCCAGAATAGAAGCCATAAAAATTCAAATCCTCAGTAAGCTGCG   300
       Q  N  T  R  Y  S  R  I  E  A  I  K  I  Q  I  L  S  K  L  R
 301  CCTGGAAACAGCTCCTAACATCAGCAAAGATGCTATAAGACAACTTCTGCCAAGAGCGCC   360
       L  E  T  A  P  [N  I  S] K  D  A  I  R  Q  L  L  P  R  A  P
 361  TCCACTCCGGGAACTGATCGATCAGTACGACGTCCAGAGGGATGACAGCAGTGATGGCTC   420
       P  L  R  E  L  I  D  Q  Y  D  V  Q  R  D  D  S  S  D  G  S
 421  TTTGGAAGATGACGATTATCACGCTACCACGGAAACAATCATTACCATGCCTACAGAGTC   480
       L  E  D  D  D  Y  H  A  T  T  E  T  I  I  T  M  P  T  E  S
 481  TGACTTTCTAATGCAAGCGGATGGCAAGCCCAAATGTTGCTTTTTTAAATTTAGCTCTAA   540
       D  F  L  M  Q  A  D  G  K  P  K  C  C  F  F  K  F  S  S  K
 541  AATACAGTACAACAAAGTAGTAAAAGCCCAACTGTGGATATATCTCAGACCCGTCAAGAC   600
       I  Q  Y  N  K  V  V  K  A  Q  L  W  I  Y  L  R  P  V  K  T
 601  TCCTACAACAGTGTTTGTGCAAATCCTGAGACTCATCAAACCCATGAAAGACGGTACAAG   660
       P  T  T  V  F  V  Q  I  L  R  L  I  K  P  M  K  D  G  T  R
 661  GTATACTGGAATCCGATCTCTGAAACTTGACATGAGCCCAGGCACTGGTATTTGGCAGAG   720
       Y  T  G  I  R  S  L  K  L  D  M  S  P  G  T  G  I  W  Q  S
 721  TATTGATGTGAAGACAGTGTTGCAAAATTGGCTCAAACAGCCTGAATCCAACTTAGGCAT   780
       I  D  V  K  T  V  L  Q  N  W  L  K  Q  P  E  S  N  L  G  I
 781  TGAAATCAAAGCTTTGGATGAGAATGGCCATGATCTTGCTGTAACCTTCCCAGGACCAGG   840
       E  I  K  A  L  D  E  N  G  H  D  L  A  V  T  F  P  G  P  G
 841  AGAAGATGGGCTGAATCCCTTTTTAGAAGTCAAGGTGACAGACACACCCAAGAGGTCCCG   900
       E  D  G  L  N  P  F  L  E  V  K  V  T  D  T  P  K [R  S  R
 901  GAGAGACTTTGGGCTTGACTGCGATGAGCACTCCACGGAATCCCGGTGCTGCCGCTACCC   960
       R] D  F  G  L  D  C  D  E  H  S  T  E  S  R  C  C  R  Y  P
 961  CCTCACGGTCGATTTTGAAGCCTTTGGATGGGACTGGATTATCGCACCCAAAAGATATAA  1020
       L  T  V  D  F  E  A  F  G  W  D  W  I  I  A  P  K  R  Y  K
1021  GGCCAATTACTGCTCAGGAGAGTGTGAATTTGTGTTTTTACAAAAATATCCGCATACTCA  1080
       A  N  Y  C  S  G  E  C  E  F  V  F  L  Q  K  Y  P  H  T  H
1081  TCTTGTGCACCAAGCAAACCCCAGAGGCTCAGCAGGCCCTTGCTGCACTCCGACAAAAAT  1140
       L  V  H  Q  A  N  P  R  G  S  A  G  P  C  C  T  P  T  K  M
1141  GTCTCCCATTAATATGCTATATTTTAATGGCAAAGAACAAATAATATATGGGAAAATTCC  1200
       S  P  I  N  M  L  Y  F  N  G  K  E  Q  I  I  Y  G  K  I  P
1201  AGCCATGGTAGTAGACCGCTGTGGGTGCTCATGAGCTTTGCATTAGGTTAGAAACTTCCC  1260
       A  M  V  V  D  R  C  G  C  S  *
```

FIG.5a

```
1261  AAGTCATGGAAGGTCTTCCCCTCAATTTCGAAACTGTGAATTCAAGCACCACAGGCTGTA  1320
1321  GGCCTTGAGTATGCTCTAGTAACGTAAGCACAAGCTACAGTGTATGAACTAAAAGAGAGA  1380
1381  ATAGATGCAATGGTTGGCATTCAACCACCAAAATAAACCATACTATAGGATGTTGTATGA  1440
1441  TTTCCAGAGTTTTTGAAATAGATGGAGATCAAATTACATTTATGTCCATATATGTATATT  1500
1501  ACAACTACAATCTAGGCAAGGAAGTGAGAGCACATCTTGTGGTCTGCTGAGTTAGGAGGG  1560
1561  TATGATTAAAAGGTAAAGTCTTATTTCCTAACAGTTTCACTTAATATTTACAGAAGAATC  1620
1621  TATATGTAGCCTTTGTAAAGTGTAGGATTGTTATCATTTAAAAACATCATGTACACTTAT  1680
1681  ATTTGTATTGTATACTTGGTAAGATAAAATTCCACAAAGTAGGAATGGGGCCTCACATAC  1740
1741  ACATTGCCATTCCTATTATAATTGGACAATCCACCACGGTGCTAATGCAGTGCTGAATGG  1800
1801  CTCCTACTGGACCTCTCGATAGAACACTCTACAAAGTACGAGTCTCTCTCTCCCTTCCAG  1860
1861  GTGCATCTCCACACACACAGCACTAAGTGTTCAATGCATTTTCTTTAAGGAAAGAAGAAT  1920
1921  CTTTTTTTCTAGAGGTCAACTTTCAGTCAACTCTAGCACAGCGGGAGTGACTGCTGCATC  1980
1981  TTAAAAGGCAGCCAAACAGTATTCATTTTTTAATCTAAATTTCAAAATCACTGTCTGCCT  2040
2041  TTATCACATGGCAATTTTGTGGTAAAATAATGGAAATGACTGGTTCTATCAATATTGTAT  2100
2101  AAAAGACTCTGAAACAATTACATTTATATAATATGTATACAATATTGTTTTGTAAATAAG  2160
2161  TGTCTCCTTTTATATTTACTTTGGTATATTTTTACACTAATGAAATTTCAAATCATTAAA  2220
2221  GTACAAAGACATGTCATGTATCACAAAAAAGGTGACTGCTTCTATTTCAGAGTGAATTAG  2280
2281  CAGATTCAATAGTGGTCTTAAAACTCTGTATGTTAAGATTAGAAGGTTATATTACAATCA  2340
2341  ATTTATGTATTTTTACATTATCAACTTATGGTTTCATGGTGGCTGTATCTATGAATGTG  2400
2401  GCTCCCAGTCAAATTTCAATGCCCCACCATTTTAAAAATTACAAGCATTACTAAACATAC  2460
2461  CAACATGTATCTAAAGAAATACAAATATGGTATCTCAATAACAGCTACTTTTTATTTTA  2520
2521  TAATTTGACAATGAATACATTTCTTTTATTTACTTCAGTTTTATAAATTGGAACTTTGTT  2580
2581  TATCAAATGTATTGTACTCATAGCTAAATGAAATTATTTCTTACATAAAAATGTGTAGAA  2640
2641  ACTATAAATTAAAGTGTTTTCACATTTTTGAAAGGC  2676
```

FIG.5b

```
  1  AAGAAAAGTAAAAGGAAGAAACAAGAACAAGAAAAAAGATTATATTGATTTTAAAATCAT   60
                                                                M
 61  GCAAAAACTGCAACTCTGTGTTTATATTTACCTGTTTATGCTGATTGTTGCTGGTCCAGT  120
      Q  K  L  Q  L  C  V  Y  I  Y  L  F  M  L  I  V  A  G  P  V
121  GGATCTAAATGAGAACAGTGAGCAAAAAGAAAATGTGGAAAAAGAGGGGCTGTGTAATGC  180
      D  L  N  E  N  S  E  Q  K  E  N  V  E  K  E  G  L  C  N  A
181  ATGTACTTGGAGACAAAACACTAAATCTTCAAGAATAGAAGCCATTAAGATACAAATCCT  240
      C  T  W  R  Q  N  T  K  S  S  R  I  E  A  I  K  I  Q  I  L
241  CAGTAAACTTCGTCTGGAAACAGCTCCTAACATCAGCAAAGATGTTATAAGACAACTTTT  300
      S  K  L  R  L  E  T  A  P [N  I  S] K  D  V  I  R  Q  L  L
301  ACCCAAAGCTCCTCCACTCCGGGAACTGATTGATCAGTATGATGTCCAGAGGGATGACAG  360
      P  K  A  P  P  L  R  E  L  I  D  Q  Y  D  V  Q  R  D  D  S
361  CAGCGATGGCTCTTTGGAAGATGACGATTATCACGCTACAACGGAAACAATCATTACCAT  420
      S  D  G  S  L  E  D  D  D  Y  H  A  T  T  E  T  I  I  T  M
421  GCCTACAGAGTCTGATTTTCTAATGCAAGTGGATGGAAAACCCAAATGTTGCTTCTTTAA  480
      P  T  E  S  D  F  L  M  Q  V  D  G  K  P  K  C  C  F  F  K
481  ATTTAGCTCTAAAATACAATACAATAAAGTAGTAAAGGCCCAACTATGGATATATTTGAG  540
      F  S  S  K  I  Q  Y  N  K  V  V  K  A  Q  L  W  I  Y  L  R
541  ACCCGTCGAGACTCCTACAACAGTGTTTGTGCAAATCCTGAGACTCATCAAACCTATGAA  600
      P  V  E  T  P  T  T  V  F  V  Q  I  L  R  L  I  K  P  M  K
601  AGACGGTACAAGGTATACTGGAATCCGATCTCTGAAACTTGACATGAACCCAGGCACTGG  660
      D  G  T  R  Y  T  G  I  R  S  L  K  L  D  M  N  P  G  T  G
661  TATTTGGCAGAGCATTGATGTGAAGACAGTGTTGCAAAATTGGCTCAAACAACCTGAATC  720
      I  W  Q  S  I  D  V  K  T  V  L  Q  N  W  L  K  Q  P  E  S
721  CAACTTAGGCATTGAAATAAAAGCTTTAGATGAGAATGGTCATGATCTTGCTGTAACCTT  780
      N  L  G  I  E  I  K  A  L  D  E  N  G  H  D  L  A  V  T  F
781  CCCAGGACCAGGAGAAGATGGGCTGAATCCGTTTTTAGAGGTCAAGGTAACAGACACACC  840
      P  G  P  G  E  D  G  L  N  P  F  L  E  V  K  V  T  D  T  P
841  AAAAAGATCCAGAAGGGATTTTGGTCTTGACTGTGATGAGCACTCAACAGAATCACGATG  900
      K [R  S  R  R] D  F  G  L  D  C  D  E  H  S  T  E  S  R  C
901  CTGTCGTTACCCTCTAACTGTGGATTTTGAAGCTTTTGGATGGGATTGGATTATCGCTCC  960
      C  R  Y  P  L  T  V  D  F  E  A  F  G  W  D  W  I  I  A  P
961  TAAAAGATATAAGGCCAATTACTGCTCTGGAGAGTGTGAATTTGTATTTTTACAAAAATA 1020
      K  R  Y  K  A  N  Y  C  S  G  E  C  E  F  V  F  L  Q  K  Y
1021 TCCTCATACTCATCTGGTACACCAAGCAAACCCCAGAGGTTCAGCAGGCCCTTGCTGTAC 1080
      P  H  T  H  L  V  H  Q  A  N  P  R  G  S  A  G  P  C  C  T
1081 TCCCACAAAGATGTCTCCAATTAATATGCTATATTTTAATGGCAAAGAACAAATAATATA 1140
      P  T  K  M  S  P  I  N  M  L  Y  F  N  G  K  E  Q  I  I  Y
1141 TGGGAAAATTCCAGCGATGGTAGTAGACCGCTGTGGGTGCTCATGAGATTTATATTAAGC 1200
      G  K  I  P  A  M  V  V  D  R  C  G  C  S  *
```

FIG. 5c

```
1201  GTTCATAACTTCCTAAAACATGGAAGGTTTTCCCCTCAACAATTTTGAAGCTGTGAAATT  1260
1261  AAGTACCACAGGCTATAGGCCTAGAGTATGCTACAGTCACTTAAGCATAAGCTACAGTAT  1320
1321  GTAAACTAAAAGGGGGAATATATGCAATGGTTGGCATTTAACCATCCAAACAAATCATAC  1380
1381  AAGAAAGTTTTATGATTTCCAGAGTTTTTGAGCTAGAAGGAGATCAAATTACATTTATGT  1440
1441  TCCTATATATTACAACATCGGCGAGGAAATGAAAGCGATTCTCCTTGAGTTCTGATGAAT  1500
1501  TAAAGGAGTATGCTTTAAAGTCTATTTCTTTAAAGTTTTGTTTAATATTTACAGAAAAAT  1560
1561  CCACATACAGTATTGGTAAAATGCAGGATTGTTATATACCATCATTCGAATCATCCTTAA  1620
1621  ACACTTGAATTTATATTGTATGGTAGTATACTTGGTAAGATAAAATTCCACAAAAATAGG  1680
1681  GATGGTGCAGCATATGCAATTTCCATTCCTATTATAATTGACACAGTACATTAACAATCC  1740
1741  ATGCCAACGGTGCTAATACGATAGGCTGAATGTCTGAGGCTACCAGGTTTATCACATAAA  1800
1801  AAACATTCAGTAAAATAGTAAGTTTCTCTTTTCTTCAGGTGCATTTTCCTACACCTCCAA  1860
1861  ATGAGGAATGGATTTTCTTTAATGTAAGAAGAATCATTTTTCTAGAGGTTGGCTTTCAAT  1920
1921  TCTGTAGCATACTTGGAGAAACTGCATTATCTTAAAAGGCAGTCAAATGGTGTTTGTTTT  1980
1981  TATCAAAATGTCAAAATAACATACTTGGAGAAGTATGTAATTTTGTCTTTGGAAAATTAC  2040
2041  AACACTGCCTTTGCAACACTGCAGTTTTTATGGTAAAATAATAGAAATGATCGACTCTAT  2100
2101  CAATATTGTATAAAAAGACTGAAACAATGCATTTATATAATATGTATACAATATTGTTTT  2160
2161  GTAAATAAGTGTCTCCTTTTTTATTTACTTTGGTATATTTTTACACTAAGGACATTTCAA  2220
2221  ATTAAGTACTAAGGCACAAAGACATGTCATGCATCACAGAAAAGCAACTACTTATATTTC  2280
2281  AGAGCAAATTAGCAGATTAAATAGTGGTCTTAAAACTCCATATGTTAATGATTAGATGGT  2340
2341  TATATTACAATCATTTTATATTTTTTACATGATTAACATTCACTTATGGATTCATGATG  2400
2401  GCTGTATAAAGTGAATTTGAAATTTCAATGGTTTACTGTCATTGTGTTTAAATCTCAACG  2460
2461  TTCCATTATTTTAATACTTGCAAAAACATTACTAAGTATACCAAAATAATTGACTCTATT  2520
2521  ATCTGAAATGAAGAATAAACTGATGCTATCTCAACAATAACTGTTACTTTTATTTTATAA  2580
2581  TTTGATAATGAATATATTTCTGCATTTATTTACTTCTGTTTTGTAAATTGGGATTTTGTT  2640
2641  AATCAAATTTATTGTACTATGACTAAATGAAATTATTTCTTACATCTAATTTGTAGAAAC  2700
2701  AGTATAAGTTATATTAAAGTGTTTTCACATTTTTTTGAAAGAC  2743
```

FIG.5d

```
  1  MMQKLQMYVYIYLFMLIAAGPVDLNEGSEREENVEKEGLCNACAWRQNTR   50
     |||||  ||||||||| ||||||||  || |||||||||||||  |||||
  1  MQKLQLCVYIYLFMLIVAGPVDLNENSEQKENVEKEGLCNACTWRQNTK    49

51  YSRIEAIKIQILSKLRLETAPNISKDAIRQLLPRAPPLRELIDQYDVQRD  100
     |||||||||||||||||||||||||| |||||| |||||||||||||||
 50  SSRIEAIKIQILSKLRLETAPNISKDVIRQLLPKAPPLRELIDQYDVQRD   99

101  DSSDGSLEDDDYHATTETIITMPTESDFLMQADGKPKCCFFKFSSKIQYN  150
     |||||||||||||||||||||||||||||||| ||||||||||||||||
100  DSSDGSLEDDDYHATTETIITMPTESDFLMQVDGKPKCCFFKFSSKIQYN  149

151  KVVKAQLWIYLRPVKTPTTVFVQILRLIKPMKDGTRYTGIRSLKLDMSPG  200
     |||||||||||||| ||||||||||||||||||||||||||||||||||
150  KVVKAQLWIYLRPVETPTTVFVQILRLIKPMKDGTRYTGIRSLKLDMNPG  199

201  TGIWQSIDVKTVLQNWLKQPESNLGIEIKALDENGHDLAVTFPGPGEDGL  250
     ||||||||||||||||||||||||||||||||||||||||||||||||||
200  TGIWQSIDVKTVLQNWLKQPESNLGIEIKALDENGHDLAVTFPGPGEDGL  249

251  NPFLEVKVTDTPKRSRRDFGLDCDEHSTESRCCRYPLTVDFEAFGWDWII  300
     |||||||||||||||||||||||||||||||||||||||||||||||||
250  NPFLEVKVTDTPKRSRRDFGLDCDEHSTESRCCRYPLTVDFEAFGWDWII  299

301  APKRYKANYCSGECEFVFLQKYPHTHLVHQANPRGSAGPCCTPTKMSPIN  350
     |||||||||||||||||||||||||||||||||||||||||||||||||
300  APKRYKANYCSGECEFVFLQKYPHTHLVHQANPRGSAGPCCTPTKMSPIN  349

351  MLYFNGKEQIIYGKIPAMVVDRCGCS                         376
     ||||||||||||||||||||||||||
350  MLYFNGKEQIIYGKIPAMVVDRCGCS                         375
```

FIG.7

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 35 base pairs
      (B) TYPE: nucleic acid (C) STRANDEDNESS: single
            (D) TOPOLOGY: linear (ii) MOLECULE TYPE: Genomic DNA (vii) IMMEDIATE SOURCE:
            (B) CLONE: SJL141

(ix) FEATURE:
            (A) NAME/KEY: Modified Base
            (B) LOCATION: 1...35
            (D) OTHER INFORMATION: /note= "N=inosine"

(xi) SEQUENCE DESCRIPTION: SEQ ID NO:1:

CCGGAATTCG GNTGGVANRA YTGGRTNRTN KCNCC                              35

(2) INFORMATION FOR SEQ ID NO:2:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: Genomic DNA (vii) IMMEDIATE SOURCE:
            (B) CLONE: SJL147

(ix) FEATURE:
            (A) NAME/KEY: CDS
            (B) LOCATION: 1...33
            (C) OTHER INFORMATION: /note= "N-inosine"

(xi) SEQUENCE DESCRIPTION: SEQ ID NO:2:

CCGGAATTCR CANSCRCARC TNTCNACNRY CAT                                33

(2) INFORMATION FOR SEQ ID NO:3:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (vii) IMMEDIATE SOURCE:
            (B) CLONE: ACM13

(ix) FEATURE:
            (A) NAME/KEY: CDS
            (B) LOCATION: 1...32

(xi) SEQUENCE DESCRIPTION: SEQ ID NO:3:

CGCGGATCCA GAAGTCAAGG TGACAGACAC AC                                 32

(2) INFORMATION FOR SEQ ID NO:4:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: Genomic DNA (vii) IMMEDIATE SOURCE:
            (B) CLONE: ACM14

(ix) FEATURE:
            (A) NAME/KEY: CDS
            (B) LOCATION: 1...33

(xi) SEQUENCE DESCRIPTION: SEQ ID NO:4:

CGCGGATCCT CCTCATGAGC ACCCACAGCG GTC                                33

(2) INFORMATION FOR SEQ ID NO:5:

(i) SEQUENCE CHARACTERISTICS:
        (A) LENGTH: 550 base pairs
        (B) TYPE: nucleic acid
        (C) STRANDEDNESS: single
        (D) TOPOLOGY: linear (vii) IMMEDIATE SOURCE:
        (B) CLONE: mouse GDF-8

(ix) FEATURE:
        (A) NAME/KEY: CDS
        (B) LOCATION: 59...436

(xi) SEQUENCE DESCRIPTION: SEQ ID NO:5:

TTAAGGTAGG AAGGATTTCA GGCTCTATTT ACATAATTGT TCTTTCCTTT TCACACAG      58

AAT CCC TTT TTA GAA GTC AAG GTG ACA GAC ACA CCC AAG AGG TCC CGG    106
Asn Pro Phe Leu Glu Val Lys Val Thr Asp Thr Pro Lys Arg Ser Arg
 1               5                  10                  15

AGA GAC TTT GGG CTT GAC TGC GAT GAG CAC TCC ACG GAA TCC CGG TGC    154
Arg Asp Phe Gly Leu Asp Cys Asp Glu His Ser Thr Glu Ser Arg Cys
             20                  25                  30

TGC CGC TAC CCC CTC ACG GTC GAT TTT GAA GCC TTT GGA TGG GAC TGG    202
Cys Arg Tyr Pro Leu Thr Val Asp Phe Glu Ala Phe Gly Trp Asp Trp
         35                  40                  45

ATT ATC GCA CCC AAA AGA TAT AAG GCC AAT TAC TGC TCA GGA GAG TGT    250
Ile Ile Ala Pro Lys Arg Tyr Lys Ala Asn Tyr Cys Ser Gly Glu Cys
     50                  55                  60

GAA TTT GTG TTT TTA CAA AAA TAT CCG CAT ACT CAT CTT GTG CAC CAA    298
Glu Phe Val Phe Leu Gln Lys Tyr Pro His Thr His Leu Val His Gln
 65                  70                  75                  80

GCA AAC CCC AGA GGC TCA GCA GGC CCT TGC TGC ACT CCG ACA AAA ATG    346
Ala Asn Pro Arg Gly Ser Ala Gly Pro Cys Cys Thr Pro Thr Lys Met
                 85                  90                  95

TCT CCC ATT AAT ATG CTA TAT TTT AAT GGC AAA GAA CAA ATA ATA TAT    394
Ser Pro Ile Asn Met Leu Tyr Phe Asn Gly Lys Glu Gln Ile Ile Tyr
                100                 105                 110

GGG AAA ATT CCA GCC ATG GTA GTA GAC CGC TGT GGG TGC TCA TGAGCTTTGC 446
Gly Lys Ile Pro Ala Met Val Val Asp Arg Cys Gly Cys Ser
            115                 120                 125

ATTAGGTTAG AAACTTCCCA AGTCATGGAA GGTCTTCCCC TCAATTTCGA AACTGTGAAT   506

TCCTGCAGCC CGGGGGATCC ACTAGTTCTA GAGCGGCCGC CACC                   550

(2) INFORMATION FOR SEQ ID NO:6:

(i) SEQUENCE CHARACTERISTICS:
        (A) LENGTH: 126 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:6:

Asn Pro Phe Leu Glu Val Lys Val Thr Asp Thr Pro Lys Arg Ser Arg
 1               5                  10                  15

Arg Asp Phe Gly Leu Asp Cys Asp Glu His Ser Thr Glu Ser Arg Cys
             20                  25                  30

```
Cys Arg Tyr Pro Leu Thr Val Asp Phe Glu Ala Phe Gly Trp Asp Trp
         35                  40                  45

Ile Ile Ala Pro Lys Arg Tyr Lys Ala Asn Tyr Cys Ser Gly Glu Cys
 50                  55                  60

Glu Phe Val Phe Leu Gln Lys Tyr Pro His Thr His Leu Val His Gln
 65                  70                  75                  80

Ala Asn Pro Arg Gly Ser Ala Gly Pro Cys Cys Thr Pro Thr Lys Met
                 85                  90                  95

Ser Pro Ile Asn Met Leu Tyr Phe Asn Gly Lys Glu Gln Ile Ile Tyr
                100                 105                 110

Gly Lys Ile Pro Ala Met Val Val Asp Arg Cys Gly Cys Ser
         115                 120                 125
```

(2) INFORMATION FOR SEQ ID NO:7:

(i) SEQUENCE CHARACTERISTICS:
        (A) LENGTH: 326 base pairs
        (B) TYPE: nucleic acid
        (C) STRANDEDNESS: single
        (D) TOPOLOGY: linear (vii) IMMEDIATE SOURCE:
        (B) CLONE: human GDF-8

(ix) FEATURE:
        (A) NAME/KEY: CDS
        (B) LOCATION: 3...326

(xi) SEQUENCE DESCRIPTION: SEQ ID NO:7:

```
CA AAA AGA TCC AGA AGG GAT TTT GGT CTT GAC TGT GAT GAG CAC TCA        47
   Lys Arg Ser Arg Arg Asp Phe Gly Leu Asp Cys Asp Glu His Ser
    1           5                  10                  15

ACA GAA TCA CGA TGC TGT CGT TAC CCT CTA ACT GTG GAT TTT GAA GCT        95
Thr Glu Ser Arg Cys Cys Arg Tyr Pro Leu Thr Val Asp Phe Glu Ala
             20                  25                  30

TTT GGA TGG GAT TGG ATT ATC GCT CCT AAA AGA TAT AAG GCC AAT TAC       143
Phe Gly Trp Asp Trp Ile Ile Ala Pro Lys Arg Tyr Lys Ala Asn Tyr
         35                  40                  45

TGC TCT GGA GAG TGT GAA TTT GTA TTT TTA CAA AAA TAT CCT CAT ACT       191
Cys Ser Gly Glu Cys Glu Phe Val Phe Leu Gln Lys Tyr Pro His Thr
     50                  55                  60

CAT CTG GTA CAC CAA GCA AAC CCC AGA GGT TCA GCA GGC CCT TGC TGT       239
His Leu Val His Gln Ala Asn Pro Arg Gly Ser Ala Gly Pro Cys Cys
 65                  70                  75

ACT CCC ACA AAG ATG TCT CCA ATT AAT ATG CTA TAT TTT AAT GGC AAA       287
Thr Pro Thr Lys Met Ser Pro Ile Asn Met Leu Tyr Phe Asn Gly Lys
 80              85                  90                  95

GAA CAA ATA ATA TAT GGG AAA ATT CCA GCG ATG GTA GTA                   326
Glu Gln Ile Ile Tyr Gly Lys Ile Pro Ala Met Val Val
                100                 105
```

(2) INFORMATION FOR SEQ ID NO:8:

(i) SEQUENCE CHARACTERISTICS:
        (A) LENGTH: 108 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:8:

Lys Arg Ser Arg Arg Asp Phe Gly Leu Asp Cys Asp Glu His Ser Thr

```
            1               5                   10                  15
        Glu Ser Arg Cys Cys Arg Tyr Pro Leu Thr Val Asp Phe Glu Ala Phe
                        20                  25                  30
        Gly Trp Asp Trp Ile Ile Ala Pro Lys Arg Tyr Lys Ala Asn Tyr Cys
                        35                  40                  45
        Ser Gly Glu Cys Glu Phe Val Phe Leu Gln Lys Tyr Pro His Thr His
                        50                  55                  60
        Leu Val His Gln Ala Asn Pro Arg Gly Ser Ala Gly Pro Cys Cys Thr
        65                      70                  75                  80
        Pro Thr Lys Met Ser Pro Ile Asn Met Leu Tyr Phe Asn Gly Lys Glu
                        85                  90                  95
        Gln Ile Ile Tyr Gly Lys Ile Pro Ala Met Val Val
                        100                 105
```

(2) INFORMATION FOR SEQ ID NO:9:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (vii) IMMEDIATE SOURCE:
        (B) CLONE: SJL141

(ix) FEATURE:
        (A) NAME/KEY: Peptide
        (B) LOCATION: 1...9
        (D) OTHER INFORMATION: /note= "Xaa at position 3=His, Gln,
            Asn, Lys, Asp or Glu; Xaa at position 4=Asp or Asn; Xaa
            at positions 6 and 7=Val, Ile or Met; Ala = Xaa at
            position 8=Ala or Ser"

(xi) SEQUENCE DESCRIPTION: SEQ ID NO:9:

```
Gly Trp Xaa Xaa Trp Xaa Xaa Xaa Pro
 1               5
```

(2) INFORMATION FOR SEQ ID NO:10:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (vii) IMMEDIATE SOURCE:
        (B) CLONE: SJL147

(ix) FEATURE:
        (A) NAME/KEY: Peptide
        (B) LOCATION: 1...8
        (D) OTHER INFORMATION: /note= "Xaa at position 2=Ile, Val,
            Met, Thr or Ala; Xaa at position 4=Asp or Glu; Xaa at
            position 7=Gly or Ala"

(xi) SEQUENCE DESCRIPTION: SEQ ID NO:10:

```
Met Xaa Val Xaa Ser Cys Xaa Cys
 1               5
```

(2) INFORMATION FOR SEQ ID NO:11:

(i) SEQUENCE CHARACTERISTICS:
        (A) LENGTH: 2676 base pairs
        (B) TYPE: nucleic acid
        (C) STRANDEDNESS: single
        (D) TOPOLOGY: linear (ii) MOLECULE TYPE: Genomic DNA (vii) IMMEDIATE SOURCE:
        (B) CLONE: Murine GDF-8

(ix) FEATURE:
        (A) NAME/KEY: CDS
        (B) LOCATION: 104...1231

(xi) SEQUENCE DESCRIPTION: SEQ ID NO:11:

```
GTCTCTCGGA CGGTACATGC ACTAATATTT CACTTGGCAT TACTCAAAAG CAAAAAGAAG          60

AAATAAGAAC AAGGGAAAAA AAAAGATTGT GCTGATTTTT AAA ATG ATG CAA AAA          115
                                               Met Met Gln Lys
                                                 1

CTG CAA ATG TAT GTT TAT ATT TAC CTG TTC ATG CTG ATT GCT GCT GGC          163
Leu Gln Met Tyr Val Tyr Ile Tyr Leu Phe Met Leu Ile Ala Ala Gly
  5              10                  15                  20

CCA GTG GAT CTA AAT GAG GGC AGT GAG AGA GAA GAA AAT GTG GAA AAA          211
Pro Val Asp Leu Asn Glu Gly Ser Glu Arg Glu Glu Asn Val Glu Lys
             25                  30                  35

GAG GGG CTG TGT AAT GCA TGT GCG TGG AGA CAA AAC ACG AGG TAC TCC          259
Glu Gly Leu Cys Asn Ala Cys Ala Trp Arg Gln Asn Thr Arg Tyr Ser
         40                  45                  50

AGA ATA GAA GCC ATA AAA ATT CAA ATC CTC AGT AAG CTG CGC CTG GAA          307
Arg Ile Glu Ala Ile Lys Ile Gln Ile Leu Ser Lys Leu Arg Leu Glu
     55                  60                  65

ACA GCT CCT AAC ATC AGC AAA GAT GCT ATA AGA CAA CTT CTG CCA AGA          355
Thr Ala Pro Asn Ile Ser Lys Asp Ala Ile Arg Gln Leu Leu Pro Arg
 70                  75                  80

GCG CCT CCA CTC CGG GAA CTG ATC GAT CAG TAC GAC GTC CAG AGG GAT          403
Ala Pro Pro Leu Arg Glu Leu Ile Asp Gln Tyr Asp Val Gln Arg Asp
 85                  90                  95                 100

GAC AGC AGT GAT GGC TCT TTG GAA GAT GAC GAT TAT CAC GCT ACC ACG          451
Asp Ser Ser Asp Gly Ser Leu Glu Asp Asp Asp Tyr His Ala Thr Thr
                105                 110                 115

GAA ACA ATC ATT ACC ATG CCT ACA GAG TCT GAC TTT CTA ATG CAA GCG          499
Glu Thr Ile Ile Thr Met Pro Thr Glu Ser Asp Phe Leu Met Gln Ala
        120                 125                 130

GAT GGC AAG CCC AAA TGT TGC TTT TTT AAA TTT AGC TCT AAA ATA CAG          547
Asp Gly Lys Pro Lys Cys Cys Phe Phe Lys Phe Ser Ser Lys Ile Gln
    135                 140                 145

TAC AAC AAA GTA GTA AAA GCC CAA CTG TGG ATA TAT CTC AGA CCC GTC          595
Tyr Asn Lys Val Val Lys Ala Gln Leu Trp Ile Tyr Leu Arg Pro Val
150                 155                 160

AAG ACT CCT ACA ACA GTG TTT GTG CAA ATC CTG AGA CTC ATC AAA CCC          643
Lys Thr Pro Thr Thr Val Phe Val Gln Ile Leu Arg Leu Ile Lys Pro
165                 170                 175                 180

ATG AAA GAC GGT ACA AGG TAT ACT GGA ATC CGA TCT CTG AAA CTT GAC          691
Met Lys Asp Gly Thr Arg Tyr Thr Gly Ile Arg Ser Leu Lys Leu Asp
                185                 190                 195

ATG AGC CCA GGC ACT GGT ATT TGG CAG AGT ATT GAT GTG AAG ACA GTG          739
Met Ser Pro Gly Thr Gly Ile Trp Gln Ser Ile Asp Val Lys Thr Val
            200                 205                 210

TTG CAA AAT TGG CTC AAA CAG CCT GAA TCC AAC TTA GGC ATT GAA ATC          787
Leu Gln Asn Trp Leu Lys Gln Pro Glu Ser Asn Leu Gly Ile Glu Ile
        215                 220                 225

AAA GCT TTG GAT GAG AAT GGC CAT GAT CTT GCT GTA ACC TTC CCA GGA          835
Lys Ala Leu Asp Glu Asn Gly His Asp Leu Ala Val Thr Phe Pro Gly
    230                 235                 240

CCA GGA GAA GAT GGG CTG AAT CCC TTT TTA GAA GTC AAG GTG ACA GAC          883
```

-continued

```
Pro Gly Glu Asp Gly Leu Asn Pro Phe Leu Glu Val Lys Val Thr Asp
245                 250                 255                 260

ACA CCC AAG AGG TCC CGG AGA GAC TTT GGG CTT GAC TGC GAT GAG CAC        931
Thr Pro Lys Arg Ser Arg Arg Asp Phe Gly Leu Asp Cys Asp Glu His
                265                 270                 275

TCC ACG GAA TCC CGG TGC TGC CGC TAC CCC CTC ACG GTC GAT TTT GAA        979
Ser Thr Glu Ser Arg Cys Cys Arg Tyr Pro Leu Thr Val Asp Phe Glu
            280                 285                 290

GCC TTT GGA TGG GAC TGG ATT ATC GCA CCC AAA AGA TAT AAG GCC AAT       1027
Ala Phe Gly Trp Asp Trp Ile Ile Ala Pro Lys Arg Tyr Lys Ala Asn
        295                 300                 305

TAC TGC TCA GGA GAG TGT GAA TTT GTG TTT TTA CAA AAA TAT CCG CAT       1075
Tyr Cys Ser Gly Glu Cys Glu Phe Val Phe Leu Gln Lys Tyr Pro His
    310                 315                 320

ACT CAT CTT GTG CAC CAA GCA AAC CCC AGA GGC TCA GCA GGC CCT TGC       1123
Thr His Leu Val His Gln Ala Asn Pro Arg Gly Ser Ala Gly Pro Cys
325                 330                 335                 340

TGC ACT CCG ACA AAA ATG TCT CCC ATT AAT ATG CTA TAT TTT AAT GGC       1171
Cys Thr Pro Thr Lys Met Ser Pro Ile Asn Met Leu Tyr Phe Asn Gly
                345                 350                 355

AAA GAA CAA ATA ATA TAT GGG AAA ATT CCA GCC ATG GTA GTA GAC CGC       1219
Lys Glu Gln Ile Ile Tyr Gly Lys Ile Pro Ala Met Val Val Asp Arg
            360                 365                 370

TGT GGG TGC TCA TGAGCTTTGC ATTAGGTTAG AAACTTCCCA AGTCATGGAA GGTCT     1276
Cys Gly Cys Ser
            375

TCCCCTCAAT TCGAAACTG TGAATTCAAG CACCACAGGC TGTAGGCCTT GAGTATGCTC      1336

TAGTAACGTA AGCACAAGCT ACAGTGTATG AACTAAAAGA GAGAATAGAT GCAATGGTTG     1396

GCATTCAACC ACCAAAATAA ACCATACTAT AGGATGTTGT ATGATTTCCA GAGTTTTTGA     1456

AATAGATGGA GATCAAATTA CATTTATGTC CATATATGTA TATTACAACT ACAATCTAGG    1516

CAAGGAAGTG AGAGCACATC TTGTGGTCTG CTGAGTTAGG AGGGTATGAT TAAAAGGTAA     1576

AGTCTTATTT CCTAACAGTT TCACTTAATA TTTACAGAAG AATCTATATG TAGCCTTTGT     1636

AAAGTGTAGG ATTGTTATCA TTTAAAAACA TCATGTACAC TTATATTTGT ATTGTATACT     1696

TGGTAAGATA AAATTCCACA AGTAGGAAT GGGGCCTCAC ATACACATTG CCATTCCTAT      1756

TATAATTGGA CAATCCACCA CGGTGCTAAT GCAGTGCTGA ATGGCTCCTA CTGGACCTCT     1816

CGATAGAACA CTCTACAAAG TACGAGTCTC TCTCTCCCTT CCAGGTGCAT CTCCACACAC     1876

ACAGCACTAA GTGTTCAATG CATTTTCTTT AAGGAAAGAA GAATCTTTTT TTCTAGAGGT     1936

CAACTTTCAG TCAACTCTAG CACAGCGGGA GTGACTGCTG CATCTTAAAA GGCAGCCAAA     1996

CAGTATTCAT TTTTTAATCT AAATTTCAAA ATCACTGTCT GCCTTTATCA CATGGCAATT     2056

TTGTGGTAAA ATAATGGAAA TGACTGGTTC TATCAATATT GTATAAAAGA CTCTGAAACA     2116

ATTACATTTA TATAATATGT ATACAATATT GTTTTGTAAA TAAGTGTCTC CTTTTATATT     2176

TACTTTGGTA TATTTTTACA CTAATGAAAT TTCAAATCAT TAAAGTACAA AGACATGTCA     2236

TGTATCACAA AAAAGGTGAC TGCTTCTATT TCAGAGTGAA TTAGCAGATT CAATAGTGGT     2296

CTTAAAACTC TGTATGTTAA GATTAGAAGG TTATATTACA ATCAATTTAT GTATTTTTA     2356

CATTATCAAC TTATGGTTTC ATGGTGGCTG TATCTATGAA TGTGGCTCCC AGTCAAATTT     2416

CAATGCCCCA CCATTTTAAA AATTACAAGC ATTACTAAAC ATACCAACAT GTATCTAAAG     2476

AAATACAAAT ATGGTATCTC AATAACAGCT ACTTTTTTAT TTTATAATTT GACAATGAAT     2536

ACATTTCTTT TATTTACTTC AGTTTTATAA ATTGGAACTT TGTTTATCAA ATGTATTGTA     2596
```

```
CTCATAGCTA AATGAAATTA TTTCTTACAT AAAAATGTGT AGAAACTATA AATTAAAGTG        2656

TTTTCACATT TTTGAAAGGC                                                    2676
```

(2) INFORMATION FOR SEQ ID NO:12:

(i) SEQUENCE CHARACTERISTICS:
        (A) LENGTH: 376 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:12:

```
Met Met Gln Lys Leu Gln Met Tyr Val Tyr Ile Tyr Leu Phe Met Leu
 1               5                  10                  15

Ile Ala Ala Gly Pro Val Asp Leu Asn Glu Gly Ser Glu Arg Glu Glu
             20                  25                  30

Asn Val Glu Lys Glu Gly Leu Cys Asn Ala Cys Ala Trp Arg Gln Asn
         35                  40                  45

Thr Arg Tyr Ser Arg Ile Glu Ala Ile Lys Ile Gln Ile Leu Ser Lys
50                  55                  60

Leu Arg Leu Glu Thr Ala Pro Asn Ile Ser Lys Asp Ala Ile Arg Gln
65                  70                  75                  80

Leu Leu Pro Arg Ala Pro Pro Leu Arg Glu Leu Ile Asp Gln Tyr Asp
                 85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
    130                 135                 140

Ser Lys Ile Gln Tyr Asn Lys Val Val Lys Ala Gln Leu Trp Ile Tyr
145                 150                 155                 160

Leu Arg Pro Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
    210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
            260                 265                 270

Cys Asp Glu His Ser Thr Glu Ser Arg Cys Cys Arg Tyr Pro Leu Thr
        275                 280                 285

Val Asp Phe Glu Ala Phe Gly Trp Asp Trp Ile Ile Ala Pro Lys Arg
    290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
```

```
                    325                 330                 335
Ala Gly Pro Cys Cys Thr Pro Thr Lys Met Ser Pro Ile Asn Met Leu
                340                 345                 350

Tyr Phe Asn Gly Lys Glu Gln Ile Ile Tyr Gly Lys Ile Pro Ala Met
            355                 360                 365

Val Val Asp Arg Cys Gly Cys Ser
        370                 375

(2) INFORMATION FOR SEQ ID NO:13:

(i) SEQUENCE CHARACTERISTICS:
        (A) LENGTH: 2743 base pairs
        (B) TYPE: nucleic acid
        (C) STRANDEDNESS: single
        (D) TOPOLOGY: linear (ii) MOLECULE TYPE: Genomic DNA (vii) IMMEDIATE SOURCE:
        (B) CLONE: Human GDF-8

(ix) FEATURE:
        (A) NAME/KEY: CDS
        (B) LOCATION: 59...1183

(xi) SEQUENCE DESCRIPTION: SEQ ID NO:13:
```

| | |
|---|---|
| AAGAAAAGTA AAAGGAAGAA ACAAGAACAA GAAAAAAGAT TATATTGATT TTAAAATC | 58 |

```
ATG CAA AAA CTG CAA CTC TGT GTT TAT ATT TAC CTG TTT ATG CTG ATT      106
Met Gln Lys Leu Gln Leu Cys Val Tyr Ile Tyr Leu Phe Met Leu Ile
  1               5                  10                  15

GTT GCT GGT CCA GTG GAT CTA AAT GAG AAC AGT GAG CAA AAA GAA AAT      154
Val Ala Gly Pro Val Asp Leu Asn Glu Asn Ser Glu Gln Lys Glu Asn
             20                  25                  30

GTG GAA AAA GAG GGG CTG TGT AAT GCA TGT ACT TGG AGA CAA AAC ACT      202
Val Glu Lys Glu Gly Leu Cys Asn Ala Cys Thr Trp Arg Gln Asn Thr
         35                  40                  45

AAA TCT TCA AGA ATA GAA GCC ATT AAG ATA CAA ATC CTC AGT AAA CTT      250
Lys Ser Ser Arg Ile Glu Ala Ile Lys Ile Gln Ile Leu Ser Lys Leu
     50                  55                  60

CGT CTG GAA ACA GCT CCT AAC ATC AGC AAA GAT GTT ATA AGA CAA CTT      298
Arg Leu Glu Thr Ala Pro Asn Ile Ser Lys Asp Val Ile Arg Gln Leu
 65                  70                  75                  80

TTA CCC AAA GCT CCT CCA CTC CGG GAA CTG ATT GAT CAG TAT GAT GTC      346
Leu Pro Lys Ala Pro Pro Leu Arg Glu Leu Ile Asp Gln Tyr Asp Val
                 85                  90                  95

CAG AGG GAT GAC AGC AGC GAT GGC TCT TTG GAA GAT GAC GAT TAT CAC      394
Gln Arg Asp Asp Ser Ser Asp Gly Ser Leu Glu Asp Asp Asp Tyr His
            100                 105                 110

GCT ACA ACG GAA ACA ATC ATT ACC ATG CCT ACA GAG TCT GAT TTT CTA      442
Ala Thr Thr Glu Thr Ile Ile Thr Met Pro Thr Glu Ser Asp Phe Leu
        115                 120                 125

ATG CAA GTG GAT GGA AAA CCC AAA TGT TGC TTC TTT AAA TTT AGC TCT      490
Met Gln Val Asp Gly Lys Pro Lys Cys Cys Phe Phe Lys Phe Ser Ser
    130                 135                 140

AAA ATA CAA TAC AAT AAA GTA GTA AAG GCC CAA CTA TGG ATA TAT TTG      538
Lys Ile Gln Tyr Asn Lys Val Val Lys Ala Gln Leu Trp Ile Tyr Leu
145                 150                 155                 160

AGA CCC GTC GAG ACT CCT ACA ACA GTG TTT GTG CAA ATC CTG AGA CTC      586
Arg Pro Val Glu Thr Pro Thr Thr Val Phe Val Gln Ile Leu Arg Leu
                165                 170                 175

ATC AAA CCT ATG AAA GAC GGT ACA AGG TAT ACT GGA ATC CGA TCT CTG      634
Ile Lys Pro Met Lys Asp Gly Thr Arg Tyr Thr Gly Ile Arg Ser Leu
```

-continued

```
                    180                 185                 190
AAA CTT GAC ATG AAC CCA GGC ACT GGT ATT TGG CAG AGC ATT GAT GTG    682
Lys Leu Asp Met Asn Pro Gly Thr Gly Ile Trp Gln Ser Ile Asp Val
            195                 200                 205

AAG ACA GTG TTG CAA AAT TGG CTC AAA CAA CCT GAA TCC AAC TTA GGC    730
Lys Thr Val Leu Gln Asn Trp Leu Lys Gln Pro Glu Ser Asn Leu Gly
    210                 215                 220

ATT GAA ATA AAA GCT TTA GAT GAG AAT GGT CAT GAT CTT GCT GTA ACC    778
Ile Glu Ile Lys Ala Leu Asp Glu Asn Gly His Asp Leu Ala Val Thr
225                 230                 235                 240

TTC CCA GGA CCA GGA GAA GAT GGG CTG AAT CCG TTT TTA GAG GTC AAG    826
Phe Pro Gly Pro Gly Glu Asp Gly Leu Asn Pro Phe Leu Glu Val Lys
                245                 250                 255

GTA ACA GAC ACA CCA AAA AGA TCC AGA AGG GAT TTT GGT CTT GAC TGT    874
Val Thr Asp Thr Pro Lys Arg Ser Arg Arg Asp Phe Gly Leu Asp Cys
        260                 265                 270

GAT GAG CAC TCA ACA GAA TCA CGA TGC TGT CGT TAC CCT CTA ACT GTG    922
Asp Glu His Ser Thr Glu Ser Arg Cys Cys Arg Tyr Pro Leu Thr Val
    275                 280                 285

GAT TTT GAA GCT TTT GGA TGG GAT TGG ATT ATC GCT CCT AAA AGA TAT    970
Asp Phe Glu Ala Phe Gly Trp Asp Trp Ile Ile Ala Pro Lys Arg Tyr
290                 295                 300

AAG GCC AAT TAC TGC TCT GGA GAG TGT GAA TTT GTA TTT TTA CAA AAA   1018
Lys Ala Asn Tyr Cys Ser Gly Glu Cys Glu Phe Val Phe Leu Gln Lys
305                 310                 315                 320

TAT CCT CAT ACT CAT CTG GTA CAC CAA GCA AAC CCC AGA GGT TCA GCA   1066
Tyr Pro His Thr His Leu Val His Gln Ala Asn Pro Arg Gly Ser Ala
                325                 330                 335

GGC CCT TGC TGT ACT CCC ACA AAG ATG TCT CCA ATT AAT ATG CTA TAT   1114
Gly Pro Cys Cys Thr Pro Thr Lys Met Ser Pro Ile Asn Met Leu Tyr
        340                 345                 350

TTT AAT GGC AAA GAA CAA ATA ATA TAT GGG AAA ATT CCA GCG ATG GTA   1162
Phe Asn Gly Lys Glu Gln Ile Ile Tyr Gly Lys Ile Pro Ala Met Val
    355                 360                 365

GTA GAC CGC TGT GGG TGC TCA TGAGATTTAT ATTAAGCGTT CATAACTTCC TAAAAC 1219
Val Asp Arg Cys Gly Cys Ser
    370                 375

ATGGAAGGTT TTCCCCTCAA CAATTTTGAA GCTGTGAAAT TAAGTACCAC AGGCTATAGG   1279

CCTAGAGTAT GCTACAGTCA CTTAAGCATA AGCTACAGTA TGTAAACTAA AAGGGGGAAT   1339

ATATGCAATG GTTGGCATTT AACCATCCAA ACAAATCATA CAAGAAAGTT TTATGATTTC   1399

CAGAGTTTTT GAGCTAGAAG GAGATCAAAT TACATTTATG TTCCTATATA TTACAACATC   1459

GGCGAGGAAA TGAAAGCGAT TCTCCTTGAG TTCTGATGAA TTAAAGGAGT ATGCTTTAAA   1519

GTCTATTTCT TTAAAGTTTT GTTTAATATT TACAGAAAAA TCCACATACA GTATTGGTAA   1579

AATGCAGGAT TGTTATATAC CATCATTCGA ATCATCCTTA AACACTTGAA TTTATATTGT   1639

ATGGTAGTAT ACTTGGTAAG ATAAAATTCC ACAAAAATAG GGATGGTGCA GCATATGCAA   1699

TTTCCATTCC TATTATAATT GACACAGTAC ATTAACAATC CATGCCAACG GTGCTAATAC   1759

GATAGGCTGA ATGTCTGAGG CTACCAGGTT TATCACATAA AAAACATTCA GTAAAATAGT   1819

AAGTTTCTCT TTTCTTCAGG TGCATTTTCC TACACCTCCA AATGAGGAAT GGATTTTCTT   1879

TAATGTAAGA AGAATCATTT TTCTAGAGGT TGGCTTTCAA TTCTGTAGCA TACTTGGAGA   1939

AACTGCATTA TCTTAAAAGG CAGTCAAATG GTGTTTGTTT TTATCAAAAT GTCAAAATAA   1999

CATACTTGGA GAAGTATGTA ATTTTGTCTT TGGAAAATTA CAACACTGCC TTTGCAACAC   2059

TGCAGTTTTT ATGGTAAAAT AATAGAAATG ATCGACTCTA TCAATATTGT ATAAAAAGAC   2119
```

```
TGAAACAATG CATTTATATA ATATGTATAC AATATTGTTT TGTAAATAAG TGTCTCCTTT      2179

TTTATTTACT TTGGTATATT TTTACACTAA GGACATTTCA AATTAAGTAC TAAGGCACAA      2239

AGACATGTCA TGCATCACAG AAAAGCAACT ACTTATATTT CAGAGCAAAT TAGCAGATTA      2299

AATAGTGGTC TTAAAACTCC ATATGTTAAT GATTAGATGG TTATATTACA ATCATTTTAT      2359

ATTTTTTTAC ATGATTAACA TTCACTTATG GATTCATGAT GGCTGTATAA AGTGAATTTG      2419

AAATTTCAAT GGTTTACTGT CATTGTGTTT AAATCTCAAC GTTCCATTAT TTAATACTT       2479

GCAAAAACAT TACTAAGTAT ACCAAAATAA TTGACTCTAT TATCTGAAAT GAAGAATAAA      2539

CTGATGCTAT CTCAACAATA ACTGTTACTT TTATTTTATA ATTTGATAAT GAATATATTT      2599

CTGCATTTAT TTACTTCTGT TTTGTAAATT GGGATTTTGT TAATCAAATT TATTGTACTA      2659

TGACTAAATG AAATTATTTC TTACATCTAA TTTGTAGAAA CAGTATAAGT TATATTAAAG      2719

TGTTTTCACA TTTTTTTGAA AGAC                                            2743
```

(2) INFORMATION FOR SEQ ID NO:14:

(i) SEQUENCE CHARACTERISTICS:
        (A) LENGTH: 375 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:14:

```
Met Gln Lys Leu Gln Leu Cys Val Tyr Ile Tyr Leu Phe Met Leu Ile
 1               5                  10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220
```

```
Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
            245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
            275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
            325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
            355                 360                 365

Val Asp Arg Cys Gly Cys Ser
370                 375
```

(2) INFORMATION FOR SEQ ID NO:15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Genomic DNA (vii) IMMEDIATE SOURCE:
        (B) CLONE: #83

(ix) FEATURE:
        (A) NAME/KEY: CDS
        (B) LOCATION: 1..34

(xi) SEQUENCE DESCRIPTION: SEQ ID NO:15:

CGCGGATCCG TGGATCTAAA TGAGAACAGT GAGC      34

(2) INFORMATION FOR SEQ ID NO:16:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: Genomic DNA (vii) IMMEDIATE SOURCE:
        (B) CLONE: #84

(ix) FEATURE:
        (A) NAME/KEY: CDS
        (B) LOCATION: 1..37

(xi) SEQUENCE DESCRIPTION: SEQ ID NO:16:

CGCGAATTCT CAGGTAATGA TTGTTTCCGT TGTAGCG      37

(2) INFORMATION FOR SEQ ID NO:17:

(i) SEQUENCE CHARACTERISTICS:
        (A) LENGTH: 20 base pairs (B) TYPE: nucleic acid
          (C) STRANDEDNESS: single
          (D) TOPOLOGY: linear (ii) MOLECULE TYPE: Genomic DNA (vii) IMMEDIATE SOURCE:
          (B) CLONE: #100

(ix) FEATURE:
          (A) NAME/KEY: CDS
          (B) LOCATION: 1..20

(xi) SEQUENCE DESCRIPTION: SEQ ID NO:17:

ACACTAAATC TTCAAGAATA                                                    20

(2) INFORMATION FOR SEQ ID NO:18:

(i) SEQUENCE CHARACTERISTICS:
          (A) LENGTH: 123 amino acids
          (B) TYPE: amino acid
          (D) TOPOLOGY: linear (ii) MOLECULE TYPE: protein (vii) IMMEDIATE SOURCE:
          (B) CLONE: GDF-1

(ix) FEATURE:
          (A) NAME/KEY: Protein
          (B) LOCATION: 1..123

(xi) SEQUENCE DESCRIPTION: SEQ ID NO:18:

Arg Pro Arg Arg Asp Ala Glu Pro Val Leu Gly Gly Pro Gly Gly
 1               5                  10                  15

Ala Cys Arg Ala Arg Arg Leu Tyr Val Ser Phe Arg Glu Val Gly Trp
                20                  25                  30

His Arg Trp Val Ile Ala Pro Arg Gly Phe Leu Ala Asn Tyr Cys Gln
            35                  40                  45

Gly Gln Cys Ala Leu Pro Val Ala Leu Ser Gly Ser Gly Gly Pro Pro
        50                  55                  60

Ala Leu Asn His Ala Val Leu Arg Ala Leu Met His Ala Ala Ala Pro
65                  70                  75                  80

Gly Ala Ala Asp Leu Pro Cys Cys Val Pro Ala Arg Leu Ser Pro Ile
                85                  90                  95

Ser Val Leu Phe Phe Asp Asn Ser Asp Asn Val Val Leu Arg Gln Tyr
               100                 105                 110

Glu Asp Met Val Val Asp Glu Cys Gly Cys Arg
            115                 120

(2) INFORMATION FOR SEQ ID NO:19:

(i) SEQUENCE CHARACTERISTICS:
          (A) LENGTH: 118 amino acids
          (B) TYPE: amino acid
          (D) TOPOLOGY: linear (ii) MOLECULE TYPE: protein (vii) IMMEDIATE SOURCE:
          (B) CLONE: BMP-2

(ix) FEATURE:
          (A) NAME/KEY: Protein
          (B) LOCATION: 1..118

(xi) SEQUENCE DESCRIPTION: SEQ ID NO:19:

```
Arg Glu Lys Arg Gln Ala Lys His Lys Gln Arg Lys Arg Leu Lys Ser
  1               5                  10                  15

Ser Cys Lys Arg His Pro Leu Tyr Val Asp Phe Ser Asp Val Gly Trp
               20                  25                  30

Asn Asp Trp Ile Val Ala Pro Pro Gly Tyr His Ala Phe Tyr Cys His
           35                   40                  45

Gly Glu Cys Pro Phe Pro Leu Ala Asp His Leu Asn Ser Thr Asn His
       50                  55                  60

Ala Ile Val Gln Thr Leu Val Asn Ser Val Asn Ser Lys Ile Pro Lys
 65                  70                  75                  80

Ala Cys Cys Val Pro Thr Glu Leu Ser Ala Ile Ser Met Leu Tyr Leu
                85                  90                  95

Asp Glu Asn Glu Lys Val Val Leu Lys Asn Tyr Gln Asp Met Val Val
                100                 105                 110

Glu Gly Cys Gly Cys Arg
            115
```

(2) INFORMATION FOR SEQ ID NO:20:

(i) SEQUENCE CHARACTERISTICS:
        (A) LENGTH: 118 amino acids
        (B) TYPE: amino acid
        (D) TOPOLOGY: linear (ii) MOLECULE TYPE: protein (vii) IMMEDIATE SOURCE:
        (B) CLONE: BMP-4

(ix) FEATURE:
        (A) NAME/KEY: Protein
        (B) LOCATION: 1..118

(xi) SEQUENCE DESCRIPTION: SEQ ID NO:20:

```
Lys Arg Ser Pro Lys His His Ser Gln Arg Ala Arg Lys Lys Asn Lys
 1               5                  10                  15

Asn Cys Arg Arg His Ser Leu Tyr Val Asp Phe Ser Asp Val Gly Trp
               20                  25                  30

Asn Asp Trp Ile Val Ala Pro Pro Gly Tyr Gln Ala Phe Tyr Cys His
           35                   40                  45

Gly Asp Cys Pro Phe Pro Leu Ala Asp His Leu Asn Ser Thr Asn His
       50                  55                  60

Ala Ile Val Gln Thr Leu Val Asn Ser Val Asn Ser Ser Ile Pro Lys
 65                  70                  75                  80

Ala Cys Cys Val Pro Thr Glu Leu Ser Ala Ile Ser Met Leu Tyr Leu
                85                  90                  95

Asp Glu Tyr Asp Lys Val Val Leu Lys Asn Tyr Gln Glu Met Val Val
                100                 105                 110

Glu Gly Cys Gly Cys Arg
            115
```

(2) INFORMATION FOR SEQ ID NO:21:

(i) SEQUENCE CHARACTERISTICS:
        (A) LENGTH: 119 amino acids
        (B) TYPE: amino acid
        (D) TOPOLOGY: linear (ii) MOLECULE TYPE: protein (vii) IMMEDIATE SOURCE:
        (B) CLONE: Vgr-1

(ix) FEATURE:
        (A) NAME/KEY: Protein
        (B) LOCATION: 1..119

(xi) SEQUENCE DESCRIPTION: SEQ ID NO:21:

Ser Arg Gly Ser Gly Ser Ser Asp Tyr Asn Gly Ser Glu Leu Lys Thr
1               5                   10                  15

Ala Cys Lys Lys His Glu Leu Tyr Val Ser Phe Gln Asp Leu Gly Trp
                20                  25                  30

Gln Asp Trp Ile Ile Ala Pro Lys Gly Tyr Ala Ala Asn Tyr Cys Asp
            35                  40                  45

Gly Glu Cys Ser Phe Pro Leu Asn Ala His Met Asn Ala Thr Asn His
    50                  55                  60

Ala Ile Val Gln Thr Leu Val His Leu Met Asn Pro Glu Tyr Val Pro
65              70                  75                  80

Lys Pro Cys Cys Ala Pro Thr Lys Leu Asn Ala Ile Ser Val Leu Tyr
                85                  90                  95

Phe Asp Asp Asn Ser Asn Val Ile Leu Lys Lys Tyr Arg Asn Met Val
            100                 105                 110

Val Arg Ala Cys Gly Cys His
            115

(2) INFORMATION FOR SEQ ID NO:22:

(i) SEQUENCE CHARACTERISTICS:
        (A) LENGTH: 119 amino acids
        (B) TYPE: amino acid
        (D) TOPOLOGY: linear (ii) MOLECULE TYPE: protein (vii) IMMEDIATE SOURCE:
        (B) CLONE: OP-1

(ix) FEATURE:
        (A) NAME/KEY: Protein
        (B) LOCATION: 1..119

(xi) SEQUENCE DESCRIPTION: SEQ ID NO:22:

Leu Arg Met Ala Asn Val Ala Glu Asn Ser Ser Asp Gln Arg Gln
1               5                   10                  15

Ala Cys Lys Lys His Glu Leu Tyr Val Ser Phe Arg Asp Leu Gly Trp
                20                  25                  30

Gln Asp Trp Ile Ile Ala Pro Glu Gly Tyr Ala Ala Tyr Tyr Cys Glu
            35                  40                  45

Gly Glu Cys Ala Phe Pro Leu Asn Ser Tyr Met Asn Ala Thr Asn His
    50                  55                  60

Ala Ile Val Gln Thr Leu Val His Phe Ile Asn Pro Glu Thr Val Pro
65              70                  75                  80

Lys Pro Cys Cys Ala Pro Thr Gln Leu Asn Ala Ile Ser Val Leu Tyr
                85                  90                  95

Phe Asp Asp Ser Ser Asn Val Ile Leu Lys Lys Tyr Arg Asn Met Val
            100                 105                 110

Val Arg Ala Cys Gly Cys His
            115

(2) INFORMATION FOR SEQ ID NO:23:

(i) SEQUENCE CHARACTERISTICS:
        (A) LENGTH: 119 amino acids

```
            (B) TYPE: amino acid
            (D) TOPOLOGY: linear (ii) MOLECULE TYPE: protein (vii) IMMEDIATE SOURCE:
            (B) CLONE: BMP-5

(ix) FEATURE:
            (A) NAME/KEY: Protein
            (B) LOCATION: 1..119

(xi) SEQUENCE DESCRIPTION: SEQ ID NO:23:

Ser Arg Met Ser Ser Val Gly Asp Tyr Asn Thr Ser Glu Gln Lys Gln
 1               5                  10                  15

Ala Cys Lys Lys His Glu Leu Tyr Val Ser Phe Arg Asp Leu Gly Trp
            20                  25                  30

Gln Asp Trp Ile Ile Ala Pro Glu Gly Tyr Ala Ala Phe Tyr Cys Asp
        35                  40                  45

Gly Glu Cys Ser Phe Pro Leu Asn Ala His Met Asn Ala Thr Asn His
50                  55                  60

Ala Ile Val Gln Thr Leu Val His Leu Met Phe Pro Asp His Val Pro
65                  70                  75                  80

Lys Pro Cys Cys Ala Pro Thr Lys Leu Asn Ala Ile Ser Val Leu Tyr
                85                  90                  95

Phe Asp Asp Ser Ser Asn Val Ile Leu Lys Lys Tyr Arg Asn Met Val
                100                 105                 110

Val Arg Ser Cys Gly Cys His
            115

(2) INFORMATION FOR SEQ ID NO:24:

(i) SEQUENCE CHARACTERISTICS:
            (A) LENGTH: 120 amino acids
            (B) TYPE: amino acid
            (D) TOPOLOGY: linear (ii) MOLECULE TYPE: protein (vii) IMMEDIATE SOURCE:
            (B) CLONE: BMP-3

(ix) FEATURE:
            (A) NAME/KEY: Protein
            (B) LOCATION: 1..120

(xi) SEQUENCE DESCRIPTION: SEQ ID NO:24:

Glu Gln Thr Leu Lys Lys Ala Arg Arg Lys Gln Trp Ile Glu Pro Arg
 1               5                  10                  15

Asn Cys Ala Arg Arg Tyr Leu Lys Val Asp Phe Ala Asp Ile Gly Trp
            20                  25                  30

Ser Glu Trp Ile Ile Ser Pro Lys Ser Phe Asp Ala Tyr Tyr Cys Ser
        35                  40                  45

Gly Ala Cys Gln Phe Pro Met Pro Lys Ser Leu Lys Pro Ser Asn His
50                  55                  60

Ala Thr Ile Gln Ser Ile Val Arg Ala Val Gly Val Val Pro Gly Ile
65                  70                  75                  80

Pro Glu Pro Cys Cys Val Pro Glu Lys Met Ser Ser Leu Ser Ile Leu
                85                  90                  95

Phe Phe Asp Glu Asn Lys Asn Val Val Leu Lys Val Tyr Pro Asn Met
                100                 105                 110

Thr Val Glu Ser Cys Ala Cys Arg
```

```
            115                 120
```

(2) INFORMATION FOR SEQ ID NO:25:

(i) SEQUENCE CHARACTERISTICS:
       (A) LENGTH: 116 amino acids
       (B) TYPE: amino acid
       (D) TOPOLOGY: linear (ii) MOLECULE TYPE: protein (vii) IMMEDIATE SOURCE:
       (B) CLONE: MIS (ix) FEATURE:
       (A) NAME/KEY: Protein
       (B) LOCATION: 1..116

(xi) SEQUENCE DESCRIPTION: SEQ ID NO:25:

```
Gly Pro Gly Arg Ala Gln Arg Ser Ala Gly Ala Thr Ala Ala Asp Gly
1               5                  10                  15

Pro Cys Ala Leu Arg Glu Leu Ser Val Asp Leu Arg Ala Glu Arg Ser
            20                  25                  30

Val Leu Ile Pro Glu Thr Tyr Gln Ala Asn Asn Cys Gln Gly Val Cys
        35                  40                  45

Gly Trp Pro Gln Ser Asp Arg Asn Pro Arg Tyr Gly Asn His Val Val
    50                  55                  60

Leu Leu Leu Lys Met Gln Ala Arg Gly Ala Ala Leu Ala Arg Pro Pro
65                  70                  75                  80

Cys Cys Val Pro Thr Ala Tyr Ala Gly Lys Leu Leu Ile Ser Leu Ser
                85                  90                  95

Glu Glu Arg Ile Ser Ala His His Val Pro Asn Met Val Ala Thr Glu
            100                 105                 110

Cys Gly Cys Arg
            115
```

(2) INFORMATION FOR SEQ ID NO:26:

(i) SEQUENCE CHARACTERISTICS:
       (A) LENGTH: 122 amino acids
       (B) TYPE: amino acid
       (D) TOPOLOGY: linear (ii) MOLECULE TYPE: protein (vii) IMMEDIATE SOURCE:
       (B) CLONE: Inhibin-alpha (ix) FEATURE:
       (A) NAME/KEY: Protein
       (B) LOCATION: 1..122

(xi) SEQUENCE DESCRIPTION: SEQ ID NO:26:

```
Ala Leu Arg Leu Leu Gln Arg Pro Pro Glu Glu Pro Ala Ala His Ala
1               5                  10                  15

Asn Cys His Arg Val Ala Leu Asn Ile Ser Phe Gln Glu Leu Gly Trp
            20                  25                  30

Glu Arg Trp Ile Val Tyr Pro Pro Ser Phe Ile Phe His Tyr Cys His
            35                  40                  45

Gly Gly Cys Gly Leu His Ile Pro Pro Asn Leu Ser Leu Pro Val Pro
    50                  55                  60

Gly Ala Pro Pro Thr Pro Ala Gln Pro Tyr Ser Leu Leu Pro Gly Ala
65                  70                  75                  80
```

-continued

```
Gln Pro Cys Cys Ala Ala Leu Pro Gly Thr Met Arg Pro Leu His Val
                 85                  90                  95

Arg Thr Thr Ser Asp Gly Gly Tyr Ser Phe Lys Tyr Glu Thr Val Pro
            100                 105                 110

Asn Leu Leu Thr Gln His Cys Ala Cys Ile
        115                 120
```

(2) INFORMATION FOR SEQ ID NO:27:

(i) SEQUENCE CHARACTERISTICS:
        (A) LENGTH: 122 amino acids
        (B) TYPE: amino acid
        (D) TOPOLOGY: linear (ii) MOLECULE TYPE: protein (vii) IMMEDIATE SOURCE:
        (B) CLONE: Inhibin-beta-alpha (ix) FEATURE:
        (A) NAME/KEY: Protein
        (B) LOCATION: 1..122

(xi) SEQUENCE DESCRIPTION: SEQ ID NO:27:

```
His Arg Arg Arg Arg Gly Leu Glu Cys Asp Gly Lys Val Asn Ile
 1               5                  10                  15

Cys Cys Lys Lys Gln Phe Phe Val Ser Phe Lys Asp Ile Gly Trp Asn
                 20                  25                  30

Asp Trp Ile Ile Ala Pro Ser Gly Tyr His Ala Asn Tyr Cys Glu Gly
             35                  40                  45

Glu Cys Pro Ser His Ile Ala Gly Thr Ser Gly Ser Ser Leu Ser Phe
 50                  55                  60

His Ser Thr Val Ile Asn His Tyr Arg Met Arg Gly His Ser Pro Phe
65                  70                  75                  80

Ala Asn Leu Lys Ser Cys Cys Val Pro Thr Lys Leu Arg Pro Met Ser
                 85                  90                  95

Met Leu Tyr Tyr Asp Asp Gly Gln Asn Ile Ile Lys Lys Asp Ile Gln
            100                 105                 110

Asn Met Ile Val Glu Glu Cys Gly Cys Ser
        115                 120
```

(2) INFORMATION FOR SEQ ID NO:28:

(i) SEQUENCE CHARACTERISTICS:
        (A) LENGTH: 121 amino acids
        (B) TYPE: amino acid
        (D) TOPOLOGY: linear (ii) MOLECULE TYPE: protein (vii) IMMEDIATE SOURCE:
        (B) CLONE: Inhibin-beta-beta (ix) FEATURE:
        (A) NAME/KEY: Protein
        (B) LOCATION: 1..121

(xi) SEQUENCE DESCRIPTION: SEQ ID NO:28:

```
His Arg Ile Arg Lys Arg Gly Leu Glu Cys Asp Gly Arg Thr Asn Leu
 1               5                  10                  15

Cys Cys Arg Gln Gln Phe Phe Ile Asp Phe Arg Leu Ile Gly Trp Asn
                 20                  25                  30

Asp Trp Ile Ile Ala Pro Thr Gly Tyr Tyr Gly Asn Tyr Cys Glu Gly
             35                  40                  45
```

```
Ser Cys Pro Ala Tyr Leu Ala Gly Val Pro Gly Ser Ala Ser Ser Phe
    50                  55                  60

His Thr Ala Val Val Asn Gln Tyr Arg Met Arg Gly Leu Asn Pro Gly
 65                  70                  75                  80

Thr Val Asn Ser Cys Cys Ile Pro Thr Lys Leu Ser Thr Met Ser Met
                 85                  90                  95

Leu Tyr Phe Asp Asp Glu Tyr Asn Ile Val Lys Arg Asp Val Pro Asn
                100                 105                 110

Met Ile Val Glu Glu Cys Gly Cys Ala
            115                 120

(2) INFORMATION FOR SEQ ID NO:29:

(i) SEQUENCE CHARACTERISTICS:
        (A) LENGTH: 115 amino acids
        (B) TYPE: amino acid
        (D) TOPOLOGY: linear (ii) MOLECULE TYPE: protein (vii) IMMEDIATE SOURCE:
        (B) CLONE: TGF-beta-1

(ix) FEATURE:
        (A) NAME/KEY: Protein
        (B) LOCATION: 1..115

(xi) SEQUENCE DESCRIPTION: SEQ ID NO:29:

His Arg Arg Ala Leu Asp Thr Asn Tyr Cys Phe Ser Ser Thr Glu Lys
  1               5                  10                  15

Asn Cys Cys Val Arg Gln Leu Tyr Ile Asp Phe Arg Lys Asp Leu Gly
                 20                  25                  30

Trp Lys Trp Ile His Glu Pro Lys Gly Tyr His Ala Asn Phe Cys Leu
             35                  40                  45

Gly Pro Cys Pro Tyr Ile Trp Ser Leu Asp Thr Gln Tyr Ser Lys Val
         50                  55                  60

Leu Ala Leu Tyr Asn Gln His Asn Pro Gly Ala Ser Ala Ala Pro Cys
 65                  70                  75                  80

Cys Val Pro Gln Ala Leu Glu Pro Leu Pro Ile Val Tyr Tyr Val Gly
                 85                  90                  95

Arg Lys Pro Lys Val Glu Gln Leu Ser Asn Met Ile Val Arg Ser Cys
                100                 105                 110

Lys Cys Ser
        115

(2) INFORMATION FOR SEQ ID NO:30:

(i) SEQUENCE CHARACTERISTICS:
        (A) LENGTH: 115 amino acids
        (B) TYPE: amino acid
        (D) TOPOLOGY: linear (ii) MOLECULE TYPE: protein (vii) IMMEDIATE SOURCE:
        (B) CLONE: TGF-beta-2

(ix) FEATURE:
        (A) NAME/KEY: Protein
        (B) LOCATION: 1..115

(xi) SEQUENCE DESCRIPTION: SEQ ID NO:30:

Lys Lys Arg Ala Leu Asp Ala Ala Tyr Cys Phe Arg Asn Val Gln Asp
```

```
           1               5                   10                  15
Asn Cys Cys Leu Arg Pro Leu Tyr Ile Asp Phe Lys Arg Asp Leu Gly
                20                  25                  30

Trp Lys Trp Ile His Glu Pro Lys Gly Tyr Asn Ala Asn Phe Cys Ala
            35                  40                  45

Gly Ala Cys Pro Tyr Leu Trp Ser Ser Asp Thr Gln His Ser Arg Val
        50                  55                  60

Leu Ser Leu Tyr Asn Thr Ile Asn Pro Glu Ala Ser Ala Ser Pro Cys
65                  70                  75                  80

Cys Val Ser Gln Asp Leu Glu Pro Leu Thr Ile Leu Tyr Tyr Ile Gly
                85                  90                  95

Lys Thr Pro Lys Ile Glu Gln Leu Ser Asn Met Ile Val Lys Ser Cys
            100                 105                 110

Lys Cys Ser
        115
```

(2) INFORMATION FOR SEQ ID NO:31:

(i) SEQUENCE CHARACTERISTICS:
        (A) LENGTH: 115 amino acids
        (B) TYPE: amino acid
        (D) TOPOLOGY: linear (ii) MOLECULE TYPE: protein (vii) IMMEDIATE SOURCE:
        (B) CLONE: TGF-beta-3

(ix) FEATURE:
        (A) NAME/KEY: Protein
        (B) LOCATION: 1..115

(xi) SEQUENCE DESCRIPTION: SEQ ID NO:31:

```
Lys Lys Arg Ala Leu Asp Thr Asn Tyr Cys Phe Arg Asn Leu Glu Glu
1               5                   10                  15

Asn Cys Cys Val Arg Pro Leu Tyr Ile Asp Phe Arg Gln Asp Leu Gly
                20                  25                  30

Trp Lys Trp Val His Glu Pro Lys Gly Tyr Tyr Ala Asn Phe Cys Ser
            35                  40                  45

Gly Pro Cys Pro Tyr Leu Arg Ser Ala Asp Thr Thr His Ser Thr Val
        50                  55                  60

Leu Gly Leu Tyr Asn Thr Leu Asn Pro Glu Ala Ser Ala Ser Pro Cys
65                  70                  75                  80

Cys Val Pro Gln Asp Leu Glu Pro Leu Thr Ile Leu Tyr Tyr Val Gly
                85                  90                  95

Arg Thr Pro Lys Val Glu Gln Leu Ser Asn Met Val Val Lys Ser Cys
            100                 105                 110

Leu Cys Ser
        115
```

(2) INFORMATION FOR SEQ ID NO:32:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..118

```
    (D) OTHER INFORMATION: /note= "Xaa at positions 2 and 3 is any
        amino acid"

(xi) SEQUENCE DESCRIPTION: SEQ ID NO:32:

Arg Xaa Xaa Arg
```

ANTIBODIES SPECIFIC FOR GROWTH DIFFERENTIATION FACTOR-8 AND METHODS OF USING SAME

This is a divisional of U.S. application Ser. No. 08/525,596, filed Oct. 26, 1995, issuing on Oct. 27, 1998 as U.S. Pat. No. 5,827,733; which is a national stage of PCT/US94/03019, filed Mar. 18, 1994 and a continuation-in-part of U.S. application Ser. No. 08/033,923, filed Mar. 19, 1993, now abandoned.

BACKGROUND OF THE INVENTION

1. Field of the Invention

The invention relates generally to growth factors and specifically to a new member of the transforming growth factor beta (TGF-β) superfamily, which is denoted, growth differentiation factor-8 (GDF-8).

2. Description of Related Art

The transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer, et al., Nature 345:167, 1990), Drosophila decapentaplegic (DPP) gene product, which is required for dorsal-ventral axis formation and morphogenesis of the imaginal disks (Padgett, et al., Nature 325:81–84, 1987), the Xenopus Vg-1 gene product, which localizes to the vegetal pole of eggs ((Weeks, et al., Cell, 51861–867, 1987), the activins (Mason, et a., Biochem, Biophys. Res. Commun., 135:957–964, 1986), which can induce the formation of mesoderm and anterior structures in Xenopus embryos (Thomsen, et al., Cell, 63:485,1990), and the bone morphogenetic proteins (BMPs, osteogenin OP-1) which can induce de novo cartilage and bone formation (Sampath, et al., J. Biol. Chem., 265:13198, 1990). The TGF-βs can influence a variety of differentiation processes, including adipogenesis, myogenesis, chondrogenesis, hematopoiesis, and epithelial cell differentiation (for review, see Massague, Cell 49:437, 1987).

The proteins of the TGF-β family are initially synthesized as a large precursor protein which subsequently undergoes proteolytic cleavage at a cluster of basic residues approximately 110–140 amino acids from the C-terminus. The C-terminal regions, or mature regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. Studies have shown that when the pro-region of a member of the TGF-β family is coexpressed with a mature region of another member of the TGF-β family, intracellular dimerization and secretion of biologically active homodimers occur (Gray, A., and Maston, A., Science, 247:1328, 1990). Additional studies by Hammonds, et al., (Molec. Endocrin. 5:149, 1991) showed that the use of the BMP-2 pro-region combined with the BMP-4 mature region led to dramatically improved expression of mature BMP-4. For most of the family members that have been studied, the homodimeric species has been found to be biologically active, but for other family members, like the inhibins (Ling, et al., Nature, 321:779, 1986) and the TGF-βs (Cheifetz, et al., Cell, 48:409, 1987), heterodimers have also been detected, and these appear to have different biological properties than the respective homodimers.

Identification of new factors that are tissue-specific in their expression pattern will provide a greater understanding of that tissue's development and function.

SUMMARY OF THE INVENTION

The present invention provides a cell growth and differentiation factor, GDF-8, a polynucleotide sequence which encodes the factor, and antibodies which are immunoreactive with the factor. This factor appears to relate to various cell proliferative disorders, especially those involving those involving muscle, nerve, and adipose tissue.

Thus, in one embodiment, the invention provides a method for detecting a cell proliferative disorder of muscle, nerve, or fat origin and which is associated with GDF-8. In another embodiment, the invention provides a method for treating a cell proliferative disorder by suppressing or enhancing GDF-8 activity.

BRIEF DESCRIPTION OF THE DRAWINGS

FIGS. 2a–b shows nucleotide and predicted amino acid sequences of murine GDF-8 (FIG. 2a; SEQ ID NO: 12) and human GDF-8 (FIG. 2b; SEQ ID NO 14). The putative dibasic processing sites in the murine sequence are boxed.

FIG. 3 shows the alignment of the C-terminal sequences of GDF-8 (see, for example, amino acids 265 to 376 of SEQ ID NO: 12) with other members of the TGF-β superfamily (SEQ ID NOS: 18 to 31). The conserved cysteine residues are boxed. Dashes denote gaps introduced in order to maximize alignment.

FIG. 4 shows amino acid homologies among different members of the TGF-β superfamily. Numbers represent percent amino acid identities between each pair calculated from the first conserved cysteine to the C-terminus. Boxes represent homologies among highly-related members within particular subgroups.

FIGS. 5a–d shows nucleotide and deduced amino acid sequences of GDF-8. A murine GDF-8 nucleotide sequence (SEQ ID NO: 11) and deduced amino acid sequence (SEQ ID NO: 12; FIG. 5a and 5b) and a human GDF-8 nucleotide sequence (SEQ ID NO: 13) and deduced amino acid sequence (SEQ ID NO: 14; FIGS. 5c and 5d) are shown. Numbers indicate nucleotide position relative to the 5' end. Consensus N-linked glycosylation signals are shaded. The putative RXXR (SEQ ID NO: 32) proteolytic cleavage sites are boxed.

FIG. 7 shows a comparison of murine and human GDF-8 amino acid sequences (SEQ ID NOS. 12 and 14, respectively). The predicted murine sequence is shown in the top lines and the predicted human sequence is shown in the bottom lines. Numbers indicate amino acid position relative to the N-terminus. Identities between the two sequences are denoted by a vertical line.

DETAILED DESCRIPTION OF THE INVENTION

Figure 1:
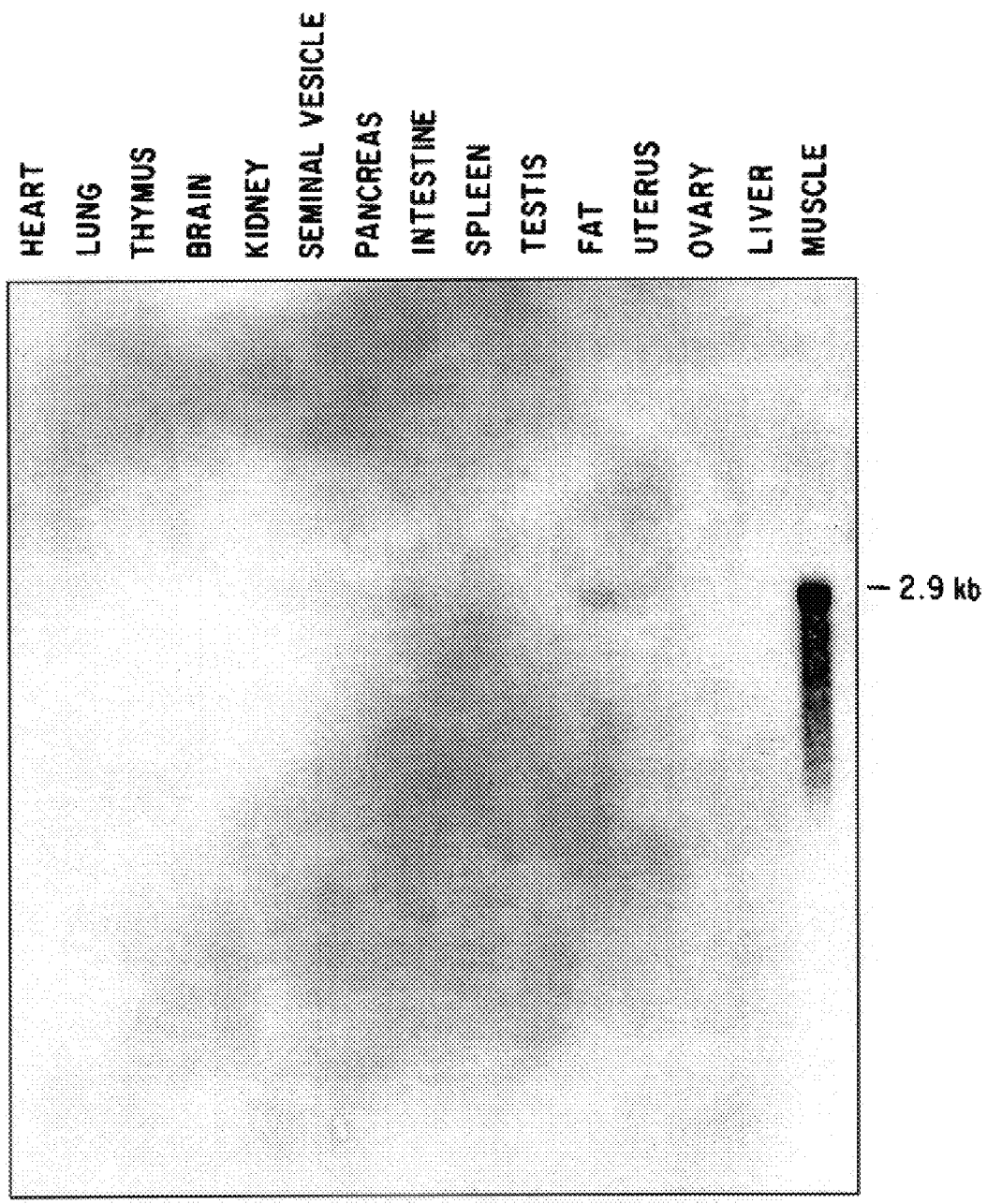
FIG. 1 is a Northern blot showing expression of GDF-8 mRNA in adult tissues. The probe was a partial murine GDF-8 clone.

The present invention provides a growth and differentiation factor, GDF-8 and a polynucleotide sequence encoding GDF-8. GDF-8 is expressed at highest levels in muscle and at lower levels in adipose tissue. In one embodiment, the invention provides a method for detection of a cell proliferative disorder of muscle, nerve, or fat origin which is associated with GDF-8 expression. In another embodiment, the invention provides a method for treating a cell proliferative disorder by using an agent which suppresses or enhances GDF-8 activity.

The TGF-β superfamily consists of multifunctional polypeptides that control proliferation, differentiation, and other functions in many cell types. Many of the peptides have regulatory, both positive and negative, effects on other peptide growth factors. The structural homology between the GDF-8 protein of this invention and the members of the TGF-β family, indicates that GDF-8 is a new member of the family of growth and differentiation factors. Based on the known activities of many of the other members, it can be expected that GDF-8 will also possess biological activities that will make it useful as a diagnostic and therapeutic reagent.

In particular, certain members of this superfamily have expression patterns or possess activities that relate to the function of the nervous system. For example, the inhibins and activins have been shown to be expressed in the brain (Meunier, et al., Proc. Natl. Acad. Sci., USA, 85:247, 1988; Sawchenko, et al., Nature, 334:615, 1988), and activin has been shown to be capable of functioning as a nerve cell survival molecule (Schubert, et al., Nature, 344:868, 1990). Another family member, namely, GDF-1, is nervous system-specific in its expression pattern (Lee, S. J., Proc. Natl. Acad. Sci., USA, 88:4250, 1991), and certain other family members, such as Vgr-1 (Lyons, et al., Proc. Natl Acad. Sci., USA, 86:4554, 1989; Jones, et al., Development, 111:531, 1991), OP-1 (Ozkaynak, et al., J. Biol. Chem., 267:25220, 1992), and BMP-4 (Jones, et al., Development, 111:531, 1991), are also known to be expressed in the nervous system. Because it is known that skeletal muscle produces a factor or factors that promote the survival of motor neurons (Brown, Trends Neurosci., 7:10, 1984), the expression of GDF-8 in muscle suggests that one activity of GDF-8 may be as a trophic factor for neurons. In this regard, GDF-8 may have applications in the treatment of neurodegenerative diseases, such as amyotrophic lateral sclerosis, or in maintaining cells or tissues in culture prior to transplantation.

GDF-8 may also have applications in treating disease processes involving muscle, such as in musculodegenerative diseases or in tissue repair due to trauma. In this regard, many other members of the TGF-β family are also important mediators of tissue repair. TGFβ has been shown to have marked effects on the formation of collagen and to cause a striking angiogenic response in the newborn mouse (Roberts, et al., Proc. Natl. Acad. Sci. USA 83:4167, 1986). TGF-β has also been shown to inhibit the differentiation of myoblasts in culture (Massague, et al., Proc. Natl. Acad. Sci., USA 83:8206, 1986). Moreover, because myoblast cells may be used as a vehicle for delivering genes to muscle for gene therapy, the properties of GDF-8 could be exploited for maintaining cells prior to transplantation or for enhancing the efficiency of the fusion process.

The expression of GDF-8 in adipose tissue also raises the possibility of applications for GDF-8 in the treatment of obesity or of disorders related to abnormal proliferation of adipocytes. In this regard, TGF-β has been shown to be a potent inhibitor of adipocyte differentiation in vitro (Ignotz and Massague, Proc. Natl. Acad. Sci., USA 82:8530, 1985).

The term "substantially pure" as used herein refers to GDF-8 which is substantially free of other proteins, lipids, carbohydrates or other materials with which it is naturally associated. One skilled in the art can purify GDF-8 using standard techniques for protein purification. The substantially pure polypeptide will yield a single major band on a non-reducing polyacylamide gel. The purity of the GDF-8 polypeptide can also be determined by amino-terminal amino acid sequence analysis. GDF-8 polypeptide includes functional fragments of the polypeptide, as long as the activity of GDF-8 remains. Smaller peptides containing the biological activity of GDF-8 are included in the invention.

The invention provides polynucleotides encoding the GDF-8 protein. These polynucleotides include DNA, cDNA and RNA sequences which encode GDF-8. It is understood that all polynucleotides encoding all or a portion of GDF-8 are also included herein, as long as they encode a polypeptide with GDF-8 activity. Such polynucleotides include naturally occurring, synthetic, and intentionally manipulated polynucleotides. For example, GDF-8 polynucleotide may be subjected to site-directed mutagenesis. The polynucleotide sequence for GDF-8 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GDF-8 polypeptide encoded by the nucleotide sequence is functionally unchanged.

Specifically disclosed herein is a genomic DNA sequence containing a portion of the GDF-8 gene. The sequence contains an open reading frame corresponding to the predicted C-terminal region of the GDF-8 precursor protein. The encoded polypeptide is predicted to contain two potential proteolytic processing sites (KR and RR). Cleavage of the precursor at the downstream site would generate a mature biologically active C-terminal fragment of 109 amino acids with a predicted molecular weight of approximately 12,400. Also, disclosed are full length murine (SEQ ID NO: 11) and human (SEQ ID NO: 13) GDF-8 cDNA sequences. The murine pre-pro-GDF-8 protein (SEQ ID NO: 12) is 376 amino acids in length, which is encoded by a 2676 base pair nucleotide sequence, beginning at nucleotide 104 and extending to a TGA stop codon at nucleotide 1232. The human GDF-8 protein (SEQ ID NO: 14) is 375 amino acids and is encoded by a 2743 base pair sequence, with the open reading frame beginning at nucleotide 59 and extending to nucleotide 1184.

The C-terminal region of GDF-8 following the putative proteolytic processing site shows significant homology to the known members of the TGF-β superfamily. The GDF-8 sequence contains most of the residues that are highly conserved in other family members (see FIG. 3). Like the TGF-βs and inhibin βs, GDF-8 contains an extra pair of cysteine residues in addition to the 7 cysteines found in virtually all other family members. Among the known family members, GDF-8 is most homologous to Vgr-1 (45% sequence identity) (see FIG. 4).

Minor modifications of the recombinant GDF-8 primary amino acid sequence may result in proteins which have substantially equivalent activity as compared to the GDF-8 polypeptide described herein. Such modifications may be deliberate, as by site-directed mutagenesis, or may be spontaneous. All of the polypeptides produced by these modifications are included herein as long as the biological activity of GDF-8 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-8 biological activity.

The nucleotide sequence encoding the GDF-8 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the GDF-8 polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981).

The development of specific DNA sequences encoding GDF-8 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., Nucl. Acid Res., 11:2325, 1983).

A cDNA expression library, such as lambda gt11, can be screened indirectly for GDF-8 peptides having at least one epitope, using antibodies specific for GDF-8. Such antibodies can be either polyclonally or monoclonally derived and used to detect expression product indicative of the presence of GDF-8 cDNA.

DNA sequences encoding GDF-8 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF-8 polynucleotide sequences may be inserted into a recombinant expression vector. The term "recombinant expression vector" refers to a plasmid, virus or other vehicle known in the art that has been manipulated by insertion or incorporation of the GDF-8 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding GDF-8 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention. Preferably, the mature C-terminal region of GDF-8 is expressed from a cDNA clone containing the entire coding sequence of GDF-8. Alternatively, the C-terminal portion of GDF-8 can be expressed as a fusion protein with the pro- region of another member of the TGF-β family or co-expressed with another pro- region (see for example, Hammonds, et al., Molec. Endocrin. 5:149, 1991; Gray, A., and Mason, A., Science, 247:1328, 1990).

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-8 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, Eukaryotic Viral Vectors, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with GDF-8 polypeptide or functional fragments thereof. Antibody which consists essentially of pooled monoclonal antibodies with differer . . . epitopic specificities, as well as distinct monoclonal antibody preparations are provided. Monoclonal antibodies are made from antigen containing fragments of the protein by methods well known to those skilled in the art (Kohler, et al., Nature, 256:495, 1975). The term antibody as used in this invention is meant to include intact molecules as well as fragments thereof, such as Fab and $F(ab')_2$, which are capable of binding an epitopic determinant on GDF-8.

The term "cell-proliferative disorder" denotes malignant as well as non-malignant cell populations which often appear to differ from the surrounding tissue both morphologically and genotypically. Malignant cells (i.e. cancer) develop as a result of a multistep process. The GDF-8 polynucleotide that is an antisense molecule is useful in treating malignancies of the various organ systems, particularly, for example, cells in muscle or adipose tissue. Essentially, any disorder which is etiologically linked to altered expression of GDF-8 could be considered susceptible to treatment with a GDF-8 suppressing reagent. One such disorder is a malignant cell proliferative disorder, for example.

The invention provides a method for detecting a cell proliferative disorder of muscle or adipose tissue which comprises contacting an anti-GDF-8 antibody with a cell suspected of having a GDF-8 associated disorder and detecting binding to the antibody. The antibody reactive with GDF-8 is labeled with a compound which allows detection of binding to GDF-8. For purposes of the invention, an antibody specific for GDF-8 polypeptide may be used to detect the level of GDF-8 in biological fluids and tissues. Any specimen containing a detectable amount of antigen can be used. A preferred sample of this invention is muscle tissue. The level of GDF-8 in the suspect cell can be compared with the level in a normal cell to determine whether the subject has a GDF-8-associated cell proliferative disorder. Preferably the subject is human.

The antibodies of the invention can be used in any subject in which it is desirable to administer in vitro or in viva immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and noncompetitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific anti-hapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in viva diagnosis is that deleterious radiation with respect to the host is minimized. Ideally, a radioisotope used for in viva imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in viva diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used in vitro and in vivo to monitor the course of amelioration of a GDF-8-associated disease in a subject Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-8-associated disease is effective. The term "ameliorate" denotes a lessening of the detrimental effect of the GDF-8-associated disease in the subject receiving therapy.

The present invention identifies a nucleotide sequence that can be expressed in an altered manner as compared to expression in a normal cell, therefore it is possible to design appropriate therapeutic or diagnostic techniques directed to this sequence. Thus, where a cell-proliferative disorder is associated with the expression of GDF-8, nucleic acid sequences that interfere with GDF-8 expression at the translational level can be used. This approach utilizes, for example, antisense nucleic acid and ribozymes to block translation of a specific GDF-8 mRNA, either by masking that mRNA with an antisense nucleic acid or by cleaving it with a ribozyme. Such disorders include neurodegenerative diseases, for example.

Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target GDF-8-producing cell. The use of antisense methods to inhibit the in vitro translation of genes is well known in the art (Marcus-Sakura, Anal.Biochem., 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J.Amer.Med. Assn., 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative or immunologic disorders which are mediated by GDF-8 protein. Such therapy would achieve its therapeutic effect by introduction of the GDF-8 antisense polynucleotide into cells having the proliferative disorder. Delivery of antisense GDF-8 polynucleotide can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-8 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the GDF-8 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to $\Psi 2$, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-8 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:.77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (1) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerois, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of GDF-8 in muscle and adipose tissue, there are a variety of applications using the polypeptide, polynucleotide, and antibodies of the invention, related to these tissues. Such applications include treatment of cell proliferative disorders involving these and other tissues, such as neural tissue. In addition, GDF-8 may be useful in various gene therapy procedures.

The data in Example 6 shows that the human GDF-8 gene is located on chromosome 2. By comparing the chromosomal location of GDF-8 with the map positions of various human disorders, it should be possible to determine whether mutations in the GDF-8 gene are involved in the etiology of human diseases. For example, an autosomal recessive form of juvenile amyotrophic lateral sclerosis has been shown to map to chromosome 2 (Hentati, et al., Neurology, 42 [Suppl.3]:201, 1992). More precise mapping of GDF-8 and analysis of DNA from these patients may indicate that GDF-8 is, in fact, the gene affected in this disease. In addition, GDF-8 is useful for distinguishing chromosome 2 from other chromosomes.

The following examples are intended to illustrate but not limit the invention. While they are typical of those that might be used, other procedures known to those skilled in the art may alternatively be used.

EXAMPLE 1

Identification and Isolation of a Novel TGF-β Family Member

To identify a new member of the TGF-β superfamily, degenerate oligonucleotides were designed which corresponded to two conserved regions among the known family members: one region spanning the two tryptophan residues conserved in all family members except MIS and the other region spanning the invariant cysteine residues near the C-terminus. These primers were used for polymerase chain reactions on mouse genomic DNA followed by subcloning the PCR products using restriction sites placed at the 5' ends of the primers, picking individual *E. coli* colonies carrying these subcloned inserts, and using a combination of random sequencing and hybridization analysis to eliminate known members of the superfamily.

GDF-8 was identified from a mixture of PCR products obtained with the primers
SJL141: 5'-CCGGAATTCGGITGG(G/C/A)A(G/A/T/C)(A/G)A(T/C)TGG(A/G)TI (A/G)TI(T/G)CICC-3' (SEQ ID NO:1)
SJL147: 5'-CCGGAATTC(G/A)CAI(G/C)C(G/A)CA(G/A)CT(G/A/T/C) TCIACI(G/A)(T/C)CAT-3' (SEQ ID NO:2)

PCR using these primers was carried out with 2 μg mouse genomic DNA at 94° C. for 1 min, 50° C. for 2 min, and 72° C. for 2 min for 40 cycles.

PCR products of approximately 280 bp were gel-purified, digested with Eco RI, gel-purified again, and subcloned in the Bluescript vector (Stratagene, San Diego, Calif.). Bacterial colonies carrying individual subclones were picked into 96 well microtiter plates, and multiple replicas were prepared by plating the cells onto nitrocellulose. The replicate filters were hybridized to probes representing known members of the family, and DNA was prepared from non-hybridizing colonies for sequence analysis.

The primer combination of SJL141 and SJL147, encoding the amino acid sequences GW(H/Q/N/K/D/E)(D/N)W(V/I/M)(V/I/M)(A/S)P (SEQ ID NO:9) and M(V/I/M/T/A)V(D/E)SC(G/A)C (SEQ ID NO:10), respectively, yielded four previously identified sequences (BMP-4, inhibin βB, GDF-3 and GDF-5) and one novel sequence, which was designated GDF-8, among 110 subclones analyzed.

Human GDF-8 was isolated using the primers:
ACM13:
5'-CGCGGATCCAGAAGTCAAGGTGACAGACACAC-3' (SEQ ID NO:3);
and
ACM14:
5'-CGCGGATCCTCCTCATGAGCACCCACAGCGGTC-3' (SEQ ID NO:4)

PCR using these primers was carried out with one μg human genomic DNA at 94° C. for 1 min, 58° C. for 2 min, and 72° C. for 2 min for 30 cycles. The PCR product was digested with Bam HI, gel-purified, and subcloned in the Bluescript vector (Stratagene, San Francisco, Calif.).

EXAMPLE 2

Expression Pattern and Sequence of GDF-8

To determine the expression pattern of GDF-8, RNA samples prepared from a variety of adult tissues were screened by Northern analysis. RNA isolation and Northern analysis were carried out as described previously (Lee, S. -J., Mol. Endocrinol., 4:1034, 1990) except that hybridization was carried out in 5× SSPE, 10% dextran sulfate, 50% formamide, 1% SDS, 200 μg/ml salmon DNA, and 0.1% each of bovine serum albumin, ficoll, and polyvinylpyrrolidone. Five micrograms of twice poly A-selected RNA prepared from each tissue (except for muscle, for which only 2 μg RNA was used) were electrophoresed on formaldehyde gels, blotted, and probed with GDF-8. As shown in FIG. 1, the GDF-8 probe detected a single mRNA species expressed at highest levels in muscle and at significantly lower levels in adipose tissue.

To obtain a larger segment of the GDF-8 gene, a mouse genomic library was screened with a probe derived from the GDF-8 PCR product. The partial sequence of a GDF-8 genomic clone is shown in FIG. 2a. The sequence contains an open reading frame corresponding to the predicted C-terminal region of the GDF-8 precursor protein. The predicted GDF-8 sequence contains two potential proteolytic processing sites, which are boxed. Cleavage of the precursor at the second of these sites would generate a mature C-terminal fragment 109 amino acids in length with a predicted molecular weight of 12,400. The partial sequence of human GDF-8 is shown in FIG. 2b. Assuming no PCR-induced errors during the isolation of the human clone, the human and mouse amino acid sequences in this region are 100% identical.

The C-terminal region of GDF-8 following the putative proteolytic processing site shows significant homology to the known members of the TGF-β superfamily (FIG. 3). FIG. 3 shows the alignment of the C-terminal sequences of GDF-8 with the corresponding regions of human GDF-1 (Lee, Proc. Natl. Acad. Sci. USA, 88:425014 4254, 1991), human BMP-2 and 4 (Wozney, et al., Science, 242:1528–1534, 1988), human Vgr-1 (Celeste, et al., Proc. Natl. Acad. Sci. USA, 87:9843–9847, 1990), human OP-1 (Ozkaynak, et al., EMBO J., 9:2085–2093, 1990), human BMP-5 (Celeste, et al., Proc. Natl. Acad. Sci. USA, 87:9843–9847, 1990), human BMP-3 (Wozney, et al., Science, 242:1528–1534,1988), human MIS (Cate, et al., Cell, 45:685–698,1986), human inhibin alpha, βA, and βB (Mason, et al., Biochem, Biophys. Res. Commun., 135:957–964, 1986), human TGF-β1 (Derynck, et al., Nature, 316:701–705, 1985), humanTGF-β2 (deMartin, et al., EMBO J., 6:3673–3677, 1987), and human TGF-β3 (ten Dijke, et al., Proc. Natl. Acad. Sci. USA, 85:4715–4719, 1988). The conserved cysteine residues are boxed. Dashes denote gaps introduced in order to maximize the alignment.

GDF-8 contains most of the residues that are highly conserved in other family members, including the seven cysteine residues with their characteristic spacing. Like the TGF-βs and inhibin βs, GDF-8 also contains two additional cysteine residues. In the case of TGF-β2, these two additional cysteine residues are known to form an intramolecular disulfide bond (Daopin, et al., Science, 257:369, 1992; Schlunegger and Grutter, Nature, 358:430, 1992).

FIG. 4 shows the amino acid homologies among the different members of the TGF-β superfamily. Numbers represent percent amino acid identities between each pair calculated from the first conserved cysteine to the C-terminus. Boxes represent homologies among highly-related members within particular subgroups. In this region, GDF-8 is most homologous to Vgr-1 (45% sequence identity).

EXAMPLE 3

Isolation of cDNA Clones Encoding Murine and Human GDF-8

In order to isolate full-length cDNA clones encoding murine and human GDF-8, cDNA libraries were prepared in the lambda ZAP II vector (Stratagene) using RNA prepared from skeletal muscle. From 5 μg of twice poly A-selected RNA prepared from murine and human muscle, cDNA libraries consisting of 4.4 million and 1.9 million recombinant phage, respectively, were constructed according to the instructions provided by Stratagene. These libraries were screened without amplification. Library screening and characterization of cDNA inserts were carried out as described previously (Lee, Mol. Endocrinol, 4:1034–1040).

Figure 6A:
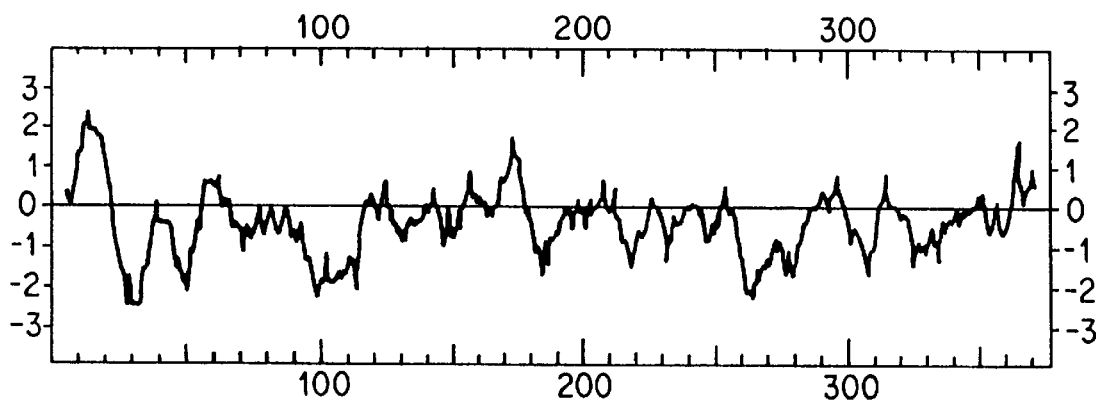
FIGS. 6a–b shows a hydropathicity profile of GDF-8. Average hydrophobicity values for murine (FIG. 6a) and human (FIG. 6b) GDF-8 were calculated using the method of Kyte and Doolittle (J. Mol. Biol., 157:105–132. 1982). Positive numbers indicate increasing hydrophobicity.

From $2.4 \times 10^6$ recombinant phage screened from the murine muscle cDNA library, greater than 280 positive phage were identified using a murine GDF-8 probe derived from a genomic clone, as described in Example 1. The entire nucleotide sequence of the longest cDNA insert analyzed is shown in FIGS. 5a and 5b and SEQ ID NO:11. The 2676 base pair sequence contains a single long open reading frame beginning with a methionine codon at nucleotide 104 and extending to a TGA stop codon at nucleotide 1232. Upstream of the putative initiating methionine codon is an in-frame stop codon at nucleotide 23. The predicted pre-pro-GDF-8 protein is 376 amino acids in length. The sequence contains a core of hydrophobic amino acids at the N-terminus suggestive of a signal peptide for secretion (FIG. 6a), one potential N-glycosylation site at asparagine 72, a putative RXXR (SEQ ID NO: 32) proteolytic cleavage site at amino acids 264–267, and a C-terminal region showing significant homology to the known members of the TGF-β superfamily. Cleavage of the precursor protein at the putative RXXR site would generate a mature C-terminal GDF-8 fragment 109 amino acids in length with a predicted molecular weight of approximately 12,400.

Figure 6B:
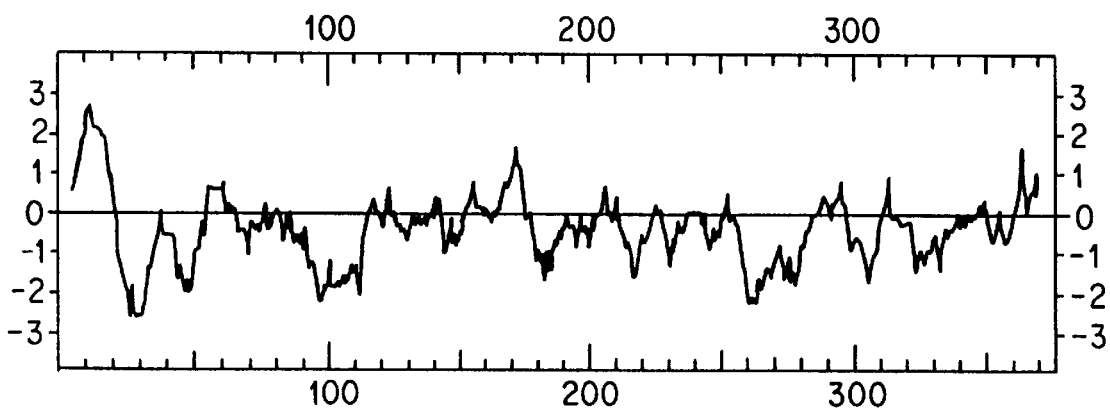

From $1.9 \times 10^6$ recombinant phage screened from the human muscle cDNA library, 4 positive phage were identified using a human GDF-8 probe derived by polymerase chain reaction on human genomic DNA. The entire nucleotide sequence of the longest cDNA insert is shown in FIGS. 5c and 5d and SEQ ID NO:13. The 2743 base pair sequence contains a single long open reading frame beginning with a methionine codon at nucleotide 59 and extending to a TGA stop codon at nucleotide 1184. The predicted pre-pro-GDF-8 protein is 375 amino acids in length. The sequence contains a core of hydrophobic amino acids at the N-terminus suggestive of a signal peptide for secretion (FIG. 6b), one potential N-glycosylation site at asparagine 71, and a putative RXXR (SEQ ID NO: 32) proteolytic cleavage site at amino acids 263–266. FIG. 7 shows a comparison of the predicted murine (top) and human (bottom) GDF-8 amino acid sequences. Numbers indicate amino acid position relative to the N-terminus. Identities between the two sequences are denoted by a vertical line. Murine and human GDF-8 are approximately 94% identical in the predicted pro-regions and 100% identical following the predicted RXXR (SEQ ID NO: 32) cleavage sites.

EXAMPLE 4

Figure 8:
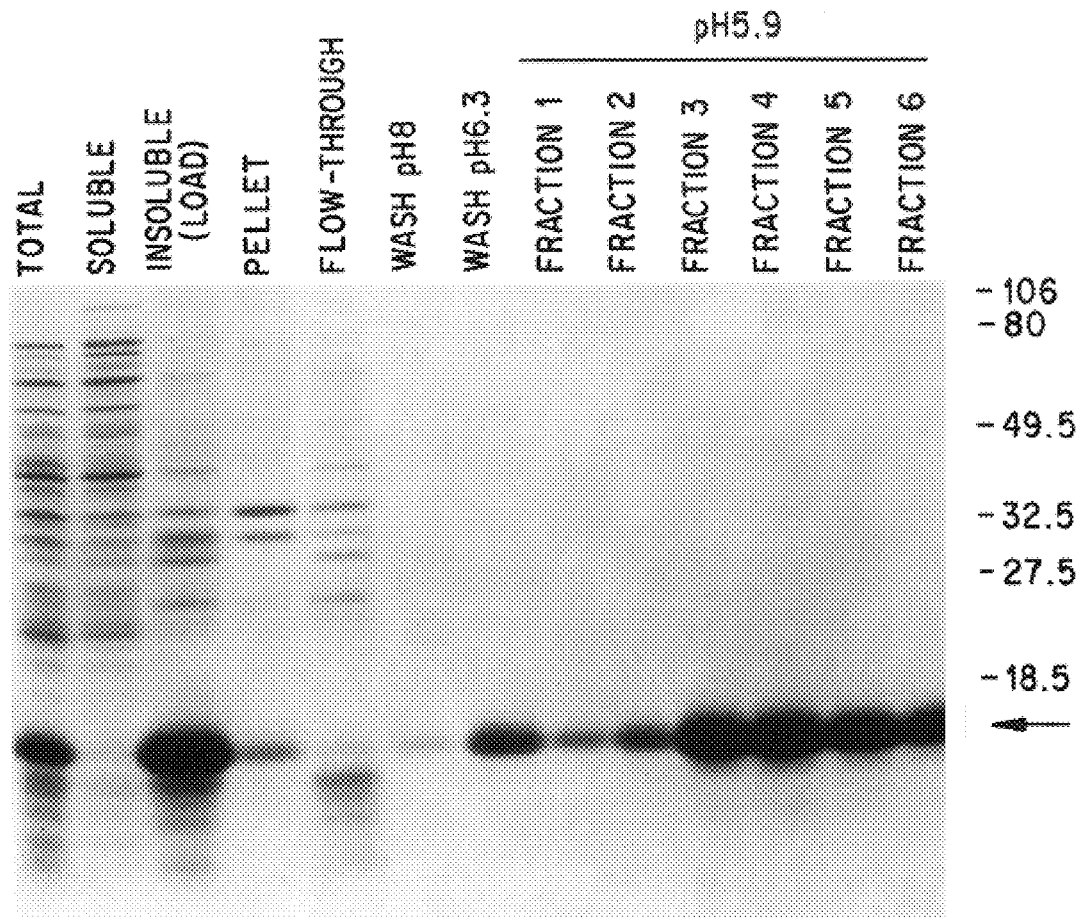
FIG. 8 shows the expression of GDF-8 in bacteria. BL21 (DE3) (pLysS) cells carrying a pRSET/GDF-8 expression plasmid were induced with isopropylthio-β-galactoside, and the GDF-8 fusion protein was purified by metal chelate chromatography. Lanes: total=total cell lysate; soluble=soluble protein fraction; insoluble=insoluble protein fraction (resuspended in 10 mM Tris pH 8.0. 50 mM sodium phosphate, 8 M urea, and 10 mM β-mercaptoethanol [buffer B]) loaded onto the column; pellet=insoluble protein fraction discarded before loading the column; flowthrough=proteins not bound by the column; washes=washes carried out in buffer B at the indicated pH's. Positions of molecular weight standards are shown at the right. Arrow indicates the position of the GDF-8 fusion protein.

Preparation of Antibodies Against GDF-8 and Expression of GDF-8 in Mammalian Cells In order to prepare antibodies against GDF-8, GDF-8 antigen was expressed as a fusion protein in bacteria. A portion of murine GDF-8 cDNA spanning amino acids 268-376 (mature region) was inserted into the pRSET vector (Invitrogen) such that the GDF-8 coding sequence was placed in frame with the initiating methionine codon present in the vector; the resulting construct created an open reading frame encoding a fusion protein with a molecular weight of approximately 16,600. The fusion construct was transformed into BL21 (DE3) (pLysS) cells, and expression of the fusion protein was induced by treatment with isopropylthio-β-galactoside as described (Rosenberg, et al., Gene, 56:125–135). The fusion protein was then purified by metal chelate chromatography according to the instructions provided by Invitrogen. A Coomassie blue-stained gel of unpurified and purified fusion proteins is shown in FIG. 8.

The purified fusion protein was used to immunize both rabbits and chickens. Immunization of rabbits was carried out by Spring Valley Labs (Sykesville, Md.), and immunization of chickens was carried out by HRP, Inc. (Denver, Pa.). Western analysis of sera both from immunized rabbits and from immunized chickens demonstrated the presence of antibodies directed against the fusion protein.

To express GDF-8 in mammalian cells, the murine GDF-8 cDNA sequence from nucleotides 48–1303 was cloned in both orientations downstream of the metallothionein I promoter in the pMSXND expression vector; this vector contains processing signals derived from SV40, a dihydrofolate reductase gene, and a gene conferring resistance to the antibiotic G418 (Lee and Nathans, J. Biol. Chem., 263:3521–3527). The resulting constructs were transfected into Chinese hamster ovary cells, and stable tranfectants were selected in the presence of G418. Two milliliters of conditioned media prepared from the G41 8-resistant cells were dialyzed, lyophilized, electrophoresed under denaturing, reducing conditions, transferred to nitrocellulose, and incubated with anti-GDF-8 antibodies (described above) and [$^{125}$I]iodoproteinA.

Figure 9:
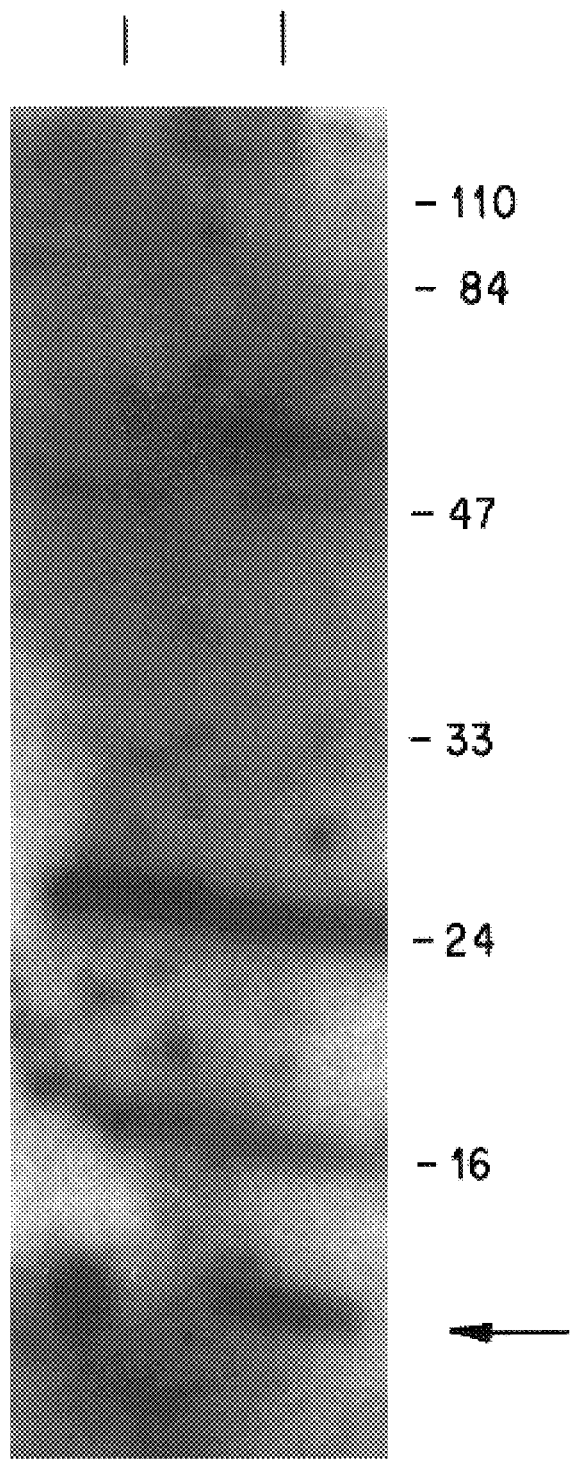
FIG. 9 shows the expression of GDF-8 in mammalian cells. Chinese hamster ovary cells were transfected with pMSXND/GDF-8 expression plasmids and selected in G418. Conditioned media from G418-resistant cells (prepared from cells transfected with constructs in which GDF-8 was cloned in either the antisense or sense orientation) were concentrated, electrophoresed under reducing conditions, blotted, and probed with anti-GDF-8 antibodies and [$^{125}$I]iodoproteinA. Arrow indicates the position of the processed GDF-8 protein.

As shown in FIG. 9, the rabbit GDF-8 antibodies (at a 1:500 dilution) detected a protein of approximately the predicted molecular weight for the mature C-terminal fragment of GDF-8 in the conditioned media of cells transfected with a construct in which GDF-8 had been cloned in the correct (sense) orientation with respect to the metallothionein promoter (lane 2); this band was not detected in a similar sample prepared from cells transfected with a control antisense construct (lane 1). Similar results were obtained using antibodies prepared in chickens. Hence, GDF-8 is secreted and proteolytically processed by these transfected mammalian cells.

EXAMPLE 5

Expression Pattern of GDF-8

Figure 10A:
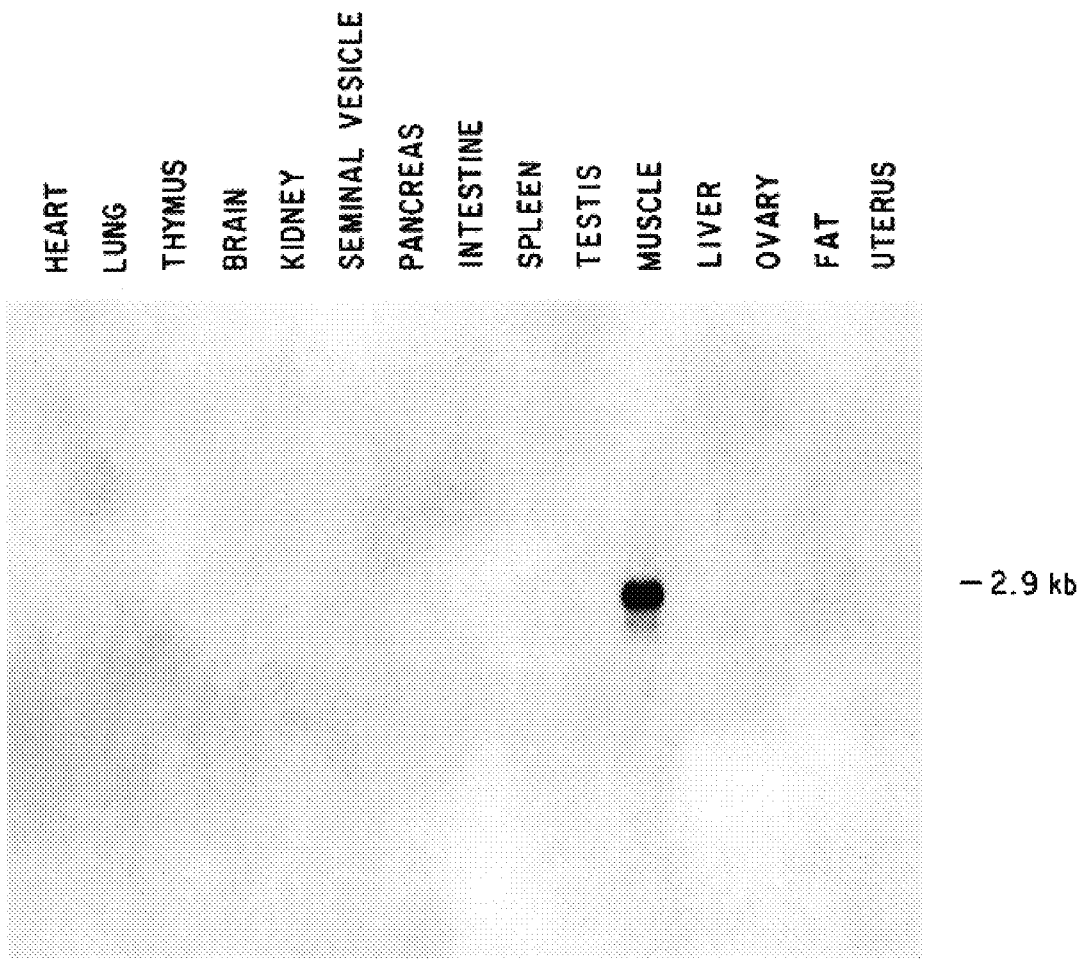
FIGS. 10a–b shows the expression of GDF-8 mRNA. Poly A-selected RNA (5 μg each) prepared from adult tissues (FIG. 10a) or placentas and embryos (FIG. 10b) at the indicated days of gestation was electrophoresed on formaldehyde gels, blotted, and probed with full length murine GDF-8.
Figure 10B:
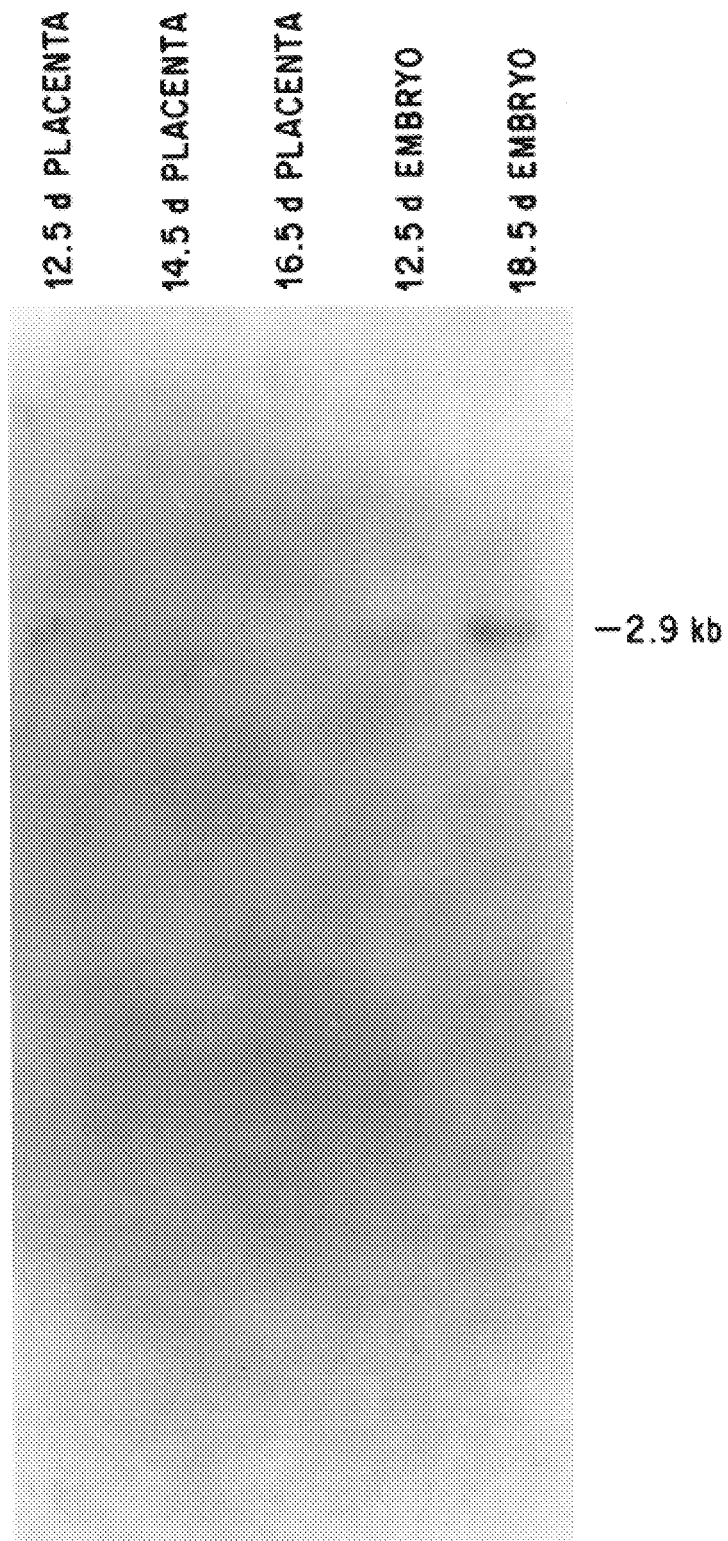

To determine the pattern of GDF-8, 5 μg of twice poly A-selected RNA prepared from a variety of murine tissue sources were subjected to Northern analysis. As shown in FIG. 10a (and as shown previously in Example 2), the GDF-8 probe detected a single mRNA species present almost exclusively in skeletal muscle among a large number of adult tissues surveyed. On longer exposures of the same blot, significantly lower but detectable levels of GDF-8 mRNA were seen in fat, brain, thymus, heart, and lung. Hence, these results confirm the high degree of specificity of GDF-8 expression in skeletal muscle. GDF-8 mRNA was also detected in mouse embryos at both gestational ages (day 12.5 and day 18.5 post-coital) examined but not in placentas at various stages of development (FIG. 10b).

EXAMPLE 6

Chromosomal Localization of GDF-8

In order to map the chromosomal location of GDF-8, DNA samples from human/rodent somatic cell hybrids (Drwinga, et al., Genomics, 16:311–413, 1993; Dubois and Naylor, Genomics, 16:315–319, 1993) were analyzed by polymerase chain reaction followed by Southern blotting. Polymerase chain reaction was carried out using primer #83, 5'-CGCGGATCCGTGGATCTAAATGAGAACAGTGAGC-3' (SEQ ID NO:15) and primer #84, 5'-CGCGAATTCTCAGGTAATGATTGTTTCCGTTGTAGCG-3' (SEQ ID NO:16) for 40 cycles at 94° C. for 2 minutes, 60° C. for 1 minute, and 72° C. for 2 minutes. These primers correspond to nucleotides 119 to 143 (flanked by a Bam H1 recognition sequence), and nucleotides 394 to 418 (flanked by an Eco R1 recognition sequence), respectively, in the human GDF-8 cDNA sequence. PCR products were electrophoresed on agarose gels, blotted, and probed with oligonucleotide #100, 5'-ACACTAAATCTTCAAGAATA-3' (SEQ ID NO:17), which corresponds to a sequence internal to the region flanked by primer #83 and #84. Filters were hybridized in 6×SSC, 1×Denhardt's solution, 100 g/ml yeast transfer RNA, and 0.05% sodium pyrophosphate at 50° C.

Figure 11:
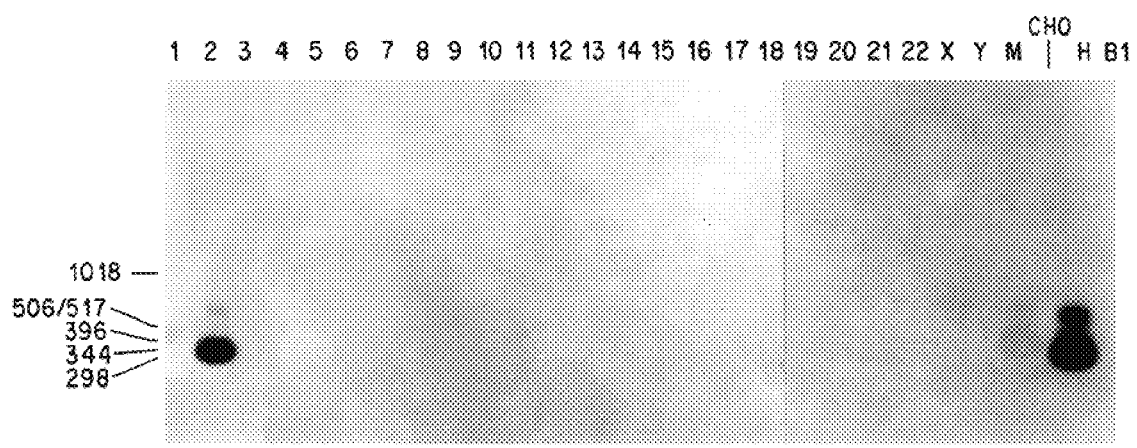
FIG. 11 shows chromosomal mapping of human GDF-8. DNA samples prepared from human/rodent somatic cell hybrid lines were subjected to PCR, electrophoresed on agarose gels, blotted, and probed. The human chromosome contained in each of the hybrid cell lines is identified at the top of each of the first 24 lanes (1–22, X, and Y). In the lanes designated M, CHO, and H, the starting DNA template was total genomic DNA from mouse, hamster, and human sources, respectively. In the lane marked B1, no template DNA was used. Numbers at left indicate the mobilities of DNA standards.

As shown in FIG. 11, the human-specific probe detected a band of the predicted size (approximately 320 base pairs) in the positive control sample (total human genomic DNA) and in a single DNA sample from the human/rodent hybrid panel. This positive signal corresponds to human chromosome 2. The human chromosome contained in each of the hybrid cell lines is identified at the top of each of the first 24 lanes (1–22, X, and Y). In the lanes designated M, CHO, and H, the starting DNA template was total genomic DNA from mouse, hamster, and human sources, respectively. In the lane marked B1, no template DNA was used. Numbers at left indicate the mobilities of DNA standards. These data show that the human GDF-8 gene is located on chromosome 2.

Although the invention has been described with reference to the presently preferred embodiment, it should be understood that various modifications can be made without departing from the spirit of the invention. Accordingly, the invention is limited only by the following claims.

SUMMARY OF SEQUENCES

SEQ ID NO: 1 is the nucleic acid sequence for clone SJL141.

SEQ ID NO: 2 is the nucleic acid sequence for clone SJL147.

SEQ ID NO: 3 is the nucleic acid sequence for clone ACM13.

SEQ ID NO: 4 is the nucleic acid sequence for clone ACM14.

SEQ ID NO: 5 is the partial nucleotide sequence and deduced amino acid sequence for murine GDF-8.

SEQ ID NO: 6 is the deduced partial amino acid sequence for murine GDF-8.

SEQ ID NO: 7 is the partial nucleotide sequence and deduced amino acid sequence for human GDF-8.

SEQ ID NO: 8 is the deduced partial amino acid sequence for human GDF-8.

SEQ ID NO: 9 is the amino acid sequence for primer SJL141.

SEQ ID NO: 10 is the amino acid sequence for primer SJL147.

SEQ ID NO: 11 is the nucleotide and deduced amino acid sequence for murine GDF-8.

SEQ ID NO: 12 is the deduced amino acid sequence for murine GDF-8.

SEQ ID NO: 13 is the nucleotide and deduced amino acid sequence for human GDF-8.

SEQ ID NO: 14 is the deduced amino acid sequence for human GDF-8.

SEQ ID NO's: 15 and 16 are nucleotide sequences for primer #83 and #84, respectively, which were used to map human GDF-8 in human/rodent somatic cell hybrids.

SEQ ID NO: 17 is the nucleotide sequence of oligonucleotide #100 which corresponds to a sequence internal to the region flanked by primer #83 and #84.

---

What is claimed is:

1. An antibody specifically reactive with growth differentiation factor-8 (GDF-8) polypeptide or an epitope thereof, said GDF-8 polypeptide comprising an amino acid sequence as set forth in SEQ ID NO: 12 or SEQ ID NO: 14.

2. The antibody of claim 1, which is a polyclonal antibody.

3. The antibody of claim 1, which is a monoclonal antibody.

4. An antibody of claim 1, wherein said GDF-8 polypeptide epitope comprises amino acids 268–376 of the amino acid sequence as set forth in SEQ ID NO: 12, or amino acids 268–375 of the amino acid sequence as set forth in SEQ ID NO: 14.

5. A method of detecting growth differentiation factor-8 (GDF-8) in a sample, comprising:

contacting the sample with an antibody specifically reactive with a GDF-8 polypeptide or an epitope thereof, said GDF-8 polypeptide comprising an amino acid sequence as set forth in SEQ ID NO: 12 or SEQ ID NO: 14; and detecting binding of the antibody to GDF-8, thereby detecting GDF-8 in the sample.

6. The method of claim 5, wherein the sample comprises a muscle cell.

7. The method of claim 5, wherein the detecting is in vivo.

8. The method of claim 5, wherein the antibody comprises a detectable label.

9. The method of claim 8, wherein the detectable label is selected from the group consisting of a radioisotope, a fluorescent compound, a bioluminescent compound and a chemiluminescent compound.

10. The method of claim 5, wherein the detecting is in vitro.

11. The method of claim 10, wherein the antibody comprises a detectable label.

12. The method of claim 11 wherein the detectable label is selected from the group consisting of a radioisotope, a fluorescent compound, a bioluminescent compound and a chemiluminescent compound.

13. The method of claim 5, wherein the sample is selected from the group consisting of a biological fluid and a tissue.

14. The method of claim 5, further comprising quantifying an amount of GDF-8 in the sample.

* * * * *